United States Patent
Pierce et al.

(10) Patent No.: US 12,257,320 B2
(45) Date of Patent: Mar. 25, 2025

(54) GENE THERAPY FOR NMNAT1-ASSOCIATED RETINAL DEGENERATION

(71) Applicant: Massachusetts Eye and Ear Infirmary, Boston, MA (US)

(72) Inventors: Eric A. Pierce, Belmont, MA (US); Luk H. Vandenberghe, Weston, MA (US); Scott Greenwald, Boston, MA (US); Emily Brown, Boston, MA (US)

(73) Assignee: Massachusetts Eye and Ear Infirmary, Boston, MA (US)

( * ) Notice: Subject to any disclaimer, the term of this patent is extended or adjusted under 35 U.S.C. 154(b) by 0 days.

(21) Appl. No.: 17/199,115

(22) Filed: Mar. 11, 2021

(65) Prior Publication Data

US 2021/0299277 A1 Sep. 30, 2021

Related U.S. Application Data

(60) Provisional application No. 62/988,260, filed on Mar. 11, 2020.

(51) Int. Cl.
*A61K 48/00* (2006.01)
*A61K 9/00* (2006.01)
*A61K 38/45* (2006.01)
*A61P 27/02* (2006.01)

(52) U.S. Cl.
CPC ........ *A61K 48/0058* (2013.01); *A61K 9/0048* (2013.01); *A61K 38/45* (2013.01); *A61K 48/0075* (2013.01); *A61P 27/02* (2018.01); *C12Y 207/07001* (2013.01)

(58) Field of Classification Search
CPC .............. A61K 48/0058; A61K 9/0048; A61K 48/0075; A61K 9/0019; A61P 27/02; C12Y 207/07001; C12N 2830/008
See application file for complete search history.

(56) References Cited

U.S. PATENT DOCUMENTS

2015/0259395 A1 9/2015 Chalberg et al.
2018/0344719 A1* 12/2018 John ...................... A61K 31/19
2019/0328761 A1 10/2019 Wu et al.

FOREIGN PATENT DOCUMENTS

| CN | 1964627 | 5/2007 |
|---|---|---|
| CN | 105980569 | 9/2016 |
| CN | 106661591 | 5/2017 |
| CN | 107206105 | 9/2017 |
| WO | WO 2018/002938 | 1/2018 |
| WO | WO 2019/025984 | 2/2019 |

OTHER PUBLICATIONS

Maguire et al (Safety and Efficacy of Gene Transfer for Leber's Congenital Amaurosis. NEJM, vol. 2240, May 2008) (Year: 2008).*
Koenekoop et al ( Mutations in NMNAT1 cause Leber congenital amaurosis and identify a new disease pathway for retinal degeneration. Nature Genetics, vol. 44, Sep. 2012, cited in the IDS dated May 21, 2021) (Year: 2012).*
Allocca et al (Novel Adeno-Associated Virus Serotypes Efficiently Transduce Murine Photoreceptors. J Virology, vol. 81, Oct. 2007). (Year: 2007).*
Karacay (Using a codon optimization tool—how it works and advantages. Integrated DNA Technologies (IDT) support & Education, Published Jul. 2018). (Year: 2018).*
Vandenberghe et al (AAV9 Targets Cone Photoreceptors in the Nonhuman Primate Retina. PLOS One, Jan. 2013) (Year: 2013).*
Greenwald et al (Mouse Models of NMNAT1-Leber Congenital Amaurosis (LCA9) Recapitulate Key Features of the Human Disease. The American Journal of Pathology, vol. 186, Jul. 2016). (Year: 2016).*
Brydon et al (AAV-Mediated Gene Augmentation Therapy Restores Critical Functions in Mutant PRPF31+/−iPSC-Derived RPE Cells. Mol Therapy, vol. 15, Dec. 2019) (Year: 2019).*
Li et al (AAV-mediated gene therapy targeting TRPV4 mechanotransduction for inhibition of pulmonary vascular leakage. APL Bioenginnering, Dec. 2019) (Year: 2019).*
Balazs et al (Antibody-based protection against HIV infection by vectored immunoprophylaxis. Nature, Jan. 2012) (Year: 2012).*
McCarty et al (Self-complementary AAV Vectors; Advances and Applications. Mol Therapy, Aug. 2008) (Year: 2008).*
Vector Builder Codon optimization tool results for Codon optimized human NMNAT1 sequence (Year: 2019).*
Vector Builder Codon optimization tool Web availability date (Year: 2019).*
Sequence alignments (Year: 2024).*
Xue, "Characterizations of NMNATI mutants, and the construction of NMNATI-LCA9 mouse model and gene therapy," China Doctoral Thesis, Zhejiang University, Jun. 15, 2018,—A human-assisted machine translation of the Xue et al.with all tables/figures translated. (Year: 2018).*
Alves & Wijnholds, "AAV gene augmentation therapy for CRB1-associated retinitis pigmentosa," Retinal Gene Therapy, Humana Press, 2018, 1715:135-151.
Belensky et al., "NAD+ metabolism in health and disease," Trends in Biochemical Sciences, 32(1):12-19.
Berger et al., "Subcellular compartmentation and differential catalytic properties of the three human nicotinamide mononucleotide adenylyltransferase isoforms," Journal of Biological Chemistry, Oct. 28, 280(43):36334-36341.
Burgess-Brown et al., "Codon optimization can improve expression of human genes in *Escherichia coli*: A multi-gene study," Protein Expression and Purification, May 2008, 59(1):94-102.
Carvalho et al., "Promising and delivering gene therapies for vision loss," Vision Research, Jun. 2015, 111:124-133.

(Continued)

*Primary Examiner* — Valarie E Bertoglio
*Assistant Examiner* — Matasha Dhar
(74) *Attorney, Agent, or Firm* — Fish & Richardson P.C.

(57) ABSTRACT

Methods and compositions for gene therapy of retinal degeneration related to mutations in nicotinamide mononucleotide adenylyltransferase 1 (NMNAT1).

18 Claims, 9 Drawing Sheets
Specification includes a Sequence Listing.

(56) References Cited

OTHER PUBLICATIONS

Chiang et al., "Exome sequencing identifies NMNAT1 mutations as a cause of Leber congenital amaurosis," Nature Genetics, Sep. 2012, 44(9):972-974.
Chiarugi et al., "The NAD metabolome—a key determinant of cancer cell biology," Nature Reviews Cancer, Nov. 2012, 12(11):741-752.
Conforti et al., "Reducing expression of NAD+ synthesizing enzyme NMNAT1 does not affect the rate of Wallerian degeneration," The FEBS Journal, Aug. 2011, 278(15):2666-2679.
Coppieters et al., "Hidden Genetic Variation in LCA9-Associated Congenital Blindness Explained by 5' UTR Mutations and Copy-Number Variations of NMNAT1," Human Mutation, Dec. 2015, 36(12):1188-1196.
Cukras et al., "Retinal AAV8-RS1 gene therapy for X-linked retinoschisis: initial findings from a phase I/IIa trial by intravitreal delivery," Molecular Therapy, Sep. 2018, 26(9):2282-2294.
Dyka et al., "Dual ABCA4-AAV Vector Treatment Reduces Pathogenic Retinal A2E Accumulation in a Mouse Model of Autosomal Recessive Stargardt Disease," Human Gene Therapy, Nov. 2019, 30(11)1361-1370.
Falk et al., "NMNAT1 mutations cause Leber congenital amaurosis," Nature Genetics, Sep. 2012, 44(9):1040-1045.
Foster et al., "Codon and mRNA sequence optimization of microdystrophin transgenes improves expression and physiological outcome in dystrophic mdx mice following AAV2/8 gene transfer," Molecular Therapy, Nov. 2008, 16(11):1825-1832.
Garavaglia et al., "Structure of human NMN adenylyltransferase: a key nuclear enzyme for NAD homeostasis," Journal of Biological Chemistry, Mar. 2002, 277(10):8524-8530.
Ghazi et al., "Treatment of retinitis pigmentosa due to MERTK mutations by ocular subretinal injection of adeno-associated virus gene vector: results of a phase I trial," Human Genetics, Mar. 2016, 135(3):327-343.
Greenwald et al., "Gene augmentation therapy preserves retinal structure and function in a mouse model of NMNAT1-associated retinal degeneration," Poster, Presented at ARVO Annual Meeting, Vancouver, CA, Apr. 28-May 2, Jul. 2019, Investigative Opthalmology & Visual Science, Jul. 2019, 1 page.
Greenwald et al., "Mouse Models of NMNAT1-Leber Congenital Amaurosis (LCA9) Recapitulate Key Features of the Human Disease," The American Journal of Pathology, Jul. 2016, 186(7):1925-1938.
Gustafsson et al., "Codon bias and heterologous protein expression," Trends in Biotechnology, Jul. 2004, 22(7):346-353.
Ill & Chiou., "Gene therapy progress and prospects: recent progress in transgene and RNAi expression cassettes," Gene Ther., May 2005, 12(10):795-802.
iovs.arovjournals.org, [online] Greenwad et al., "Gene augmentation therapy for NMNAT1-associated retinal degeneration: Promise and challenges," available no later than Jul. 2019, retrieved from URL <https://iovs.arvojournals.org/article.aspx?articleid=2743252&resultClick=1>, 2 pages.
Koenekoop et al., "Mutations in NMNAT1 cause Leber congenital amaurosis and identify a new disease pathway for retinal degeneration," Nature Genetics, Sep. 2012, 44(9):1035-1040.
Lam et al., "Choroideremia gene therapy phase 2 clinical trial: 24-month results," American Journal of Opthalmology, Jan. 2019, 197:65-73.
Lau et al., "The NMN/NaMN adenylyltransferase (NMNAT) protein family," Fron. Biosci., Jan. 2009, 14:410-431.
Lloyd et al., "Estimation of impact of RPE65-mediated inherited retinal disease on quality of life and the potential benefits of gene therapy," British Journal of Ophthalmology, Nov. 2019, 103(11):1610-1614.
McCarty et al., "Self-complementary recombinant adeno-associated virus (scAAV) vectors promote efficient transduction independently of DNA synthesis," Gene Therapy, 8(16):1248-1254.
McCarty, "Self-complementary AAV vectors; advances and applications," Molecular Therapy, Oct. 2008, 16(10):1648-1656.
McCullough et al., "Somatic gene editing of GUCY2D by AAV-CRISPR/Cas9 alters retinal structure and function in mouse and macaque," Human Gene Therapy, May 2019, 30(5):571-589.
Nash et al., "NMNAT1 variants cause cone and cone-rod dystrophy," European Journal of Human Genetics, Mar. 2018, 26(3):428-433.
Ofri et al., "Six years and counting: restoration of photopic retinal function and visual behavior following gene augmentation therapy in a sheep model of CNGA3 achromatopsia," Human Gene Therapy, Dec. 2018, 29(12):1376-1386.
Ong et al., "Adeno-associated viral gene therapy for inherited retinal disease," Pharmaceutical Research, Feb. 2019, 36(2):34, 13 pages.
Perrault et al., "Mutations in NMNAT1 cause Leber congenital amaurosis with early-onset severe macular and optic atrophy," Nature Genetics, Sep. 2012, 44(9):975-977.
Sack et al., "Transient B cell depletion or improved transgene expression by codon optimization promote tolerance to factor VIII in gene therapy," PloS One, May 2012, 7(5):e37671.
Sasaki et al., "Characterization of Leber congenital amaurosis-associated NMNAT1 mutants," Journal of Biological Chemistry, Jul. 2015, 290(28):17228-17238.
Greenwald et al., "Gene Therapy Preserves Retinal Structure and Function in a Mouse Model of NMNAT1-Associated Retinal Degeneration," Molecular Therapy Methods & Clinical Development, 2020, 18:582-594.
International Search Report and Written Opinion in International Appln. No. PCT/US2021/021936, dated Jun. 24, 2021, 11 pages.
Brown et al., "Reduced nuclear $NAD^+$ drives DNA damage and subsequent immune activation in the retina," Hum Mol Genet, May 2022, 31(9):1370-1388.
International Preliminary Report on Patentability in International Appln. No. PCT/US2021/021936, mailed on Sep. 22, 2022, 8 pages.
Petit et al., "Rod Outer Segment Development Influences AAV-Mediated Photoreceptor Transduction After Subretinal Injection," Hum Gene Ther., Jun. 2017, 28(6):464-481.
Bush and Sieving, "Abstract: Inner retinal contributions to the primate photopic fast flicker electroretinogram," J Opt Soc Am A Opt Image Sci Vis, Mar. 1996, 13(3):557-565, 1 page.
Carter et al., "Adenovirus-associated virus multiplication. IX. Extent of transcription of the viral genome in vivo," J Virol, Dec. 1972, 10(6):1118-1125.
Carter-Dawson and LaVail, "Abstract: Rods and cones in the mouse retina. II. Autoradiographic analysis of cell generation using tritiated thymidine," J Comp Neurol, Nov. 1979, 188(2):263-272, 1 page.
Dalkara et al., "In vivo-directed evolution of a new adeno-associated virus for therapeutic outer retinal gene delivery from the vitreous," Sci Transl Med, Jun. 2013, 5(189):189ra176, 12 pages.
Dunn et al., "Abstract: ARPE-19, a human retinal pigment epithelial cell line with differentiated properties," Exp Eye Res, Feb. 1996, 62(2):155-169, 2 pages.
Geller and Sieving, "Assessment of foveal cone photoreceptors in Stargardt's macular dystrophy using a small dot detection task," Vision Res, Jul. 1993, 33(11):1509-1524.
Geller et al., "Abstract: Effect on grating identification of sampling with degenerate arrays," J Opt Soc Am A, Mar. 1992, 9(3):472-477, 1 page.
Greenwald et al., "S-opsin knockout mice with the endogenous M-opsin gene replaced by an L-opsin variant," Vis Neurosci, Jan. 2014, 31(1):25-37, 31 pages.
Kim et al., "High cleavage efficiency of a 2A peptide derived from porcine teschovirus-1 in human cell lines, zebrafish and mice," PLoS One, 2011, 6(4):e18556, 8 pages.
Koehn et al., "Ketamine/Xylazine-Induced Corneal Damage in Mice," PLoS One, Jul. 2015, 10(7):e0132804, 12 pages.
Patrício et al., "Inclusion of the Woodchuck Hepatitis Virus Post-transcriptional Regulatory Element Enhances AAV2-Driven Transduction of Mouse and Human Retina," Mol Ther Nucleic Acids, Mar. 2017, 6:198-208.

(56) References Cited

OTHER PUBLICATIONS

Pawlyk et al., "Replacement gene therapy with a human RPGRIP1 sequence slows photoreceptor degeneration in a murine model of Leber congenital amaurosis," Hum Gene Ther, Aug. 2010, 21(8):993-1004.
Phifer and Terry, "Abstract: Use of hypothermia for general anesthesia in preweanling rodents," Physiol Behav, 1986, 38(6):887-890, 1 page.
Saito et al., "Abstract: Intravitreal cellular infiltrate imaged as punctate spots by spectral-domain optical coherence tomography in eyes with posterior segment inflammatory disease," Retina, Mar. 2013, 33(3):559-565, 1 page.
Sipo et al., "Differential internalization and nuclear uncoating of self-complementary adeno-associated virus pseudotype vectors as determinants of cardiac cell transduction," Gene Ther, Sep. 2007, 14(18):1319-1329.
Stockton and Slaughter, "B-wave of the electroretinogram. A reflection of ON bipolar cell activity," J Gen Physiol, Jan. 1989, 93(1):101-122.
Turner and Albassam, "Susceptibility of rats to corneal lesions after injectable anesthesia," Comp Med, Apr. 2005, 55(2):175-182.
Wang et al., "Existence of transient functional double-stranded DNA intermediates during recombinant AAV transduction," Proc Natl Acad Sci U S A, Aug. 2007, 104(32):13104-13109.
Xiong et al., "NRF2 promotes neuronal survival in neurodegeneration and acute nerve damage," J Clin Invest, Apr. 2015, 125(4):1433-1445.
Xiong et al., "AAV cis-regulatory sequences are correlated with ocular toxicity," Proc Natl Acad Sci U S A, Mar. 2019, 116(12):5785-5794.
Zarranz-Ventura et al., "Evaluation of Objective Vitritis Grading Method Using Optical Coherence Tomography: Influence of Phakic Status and Previous Vitrectomy," Am J Ophthalmol, Jan. 2016, 161:172-180.e171-174, 30 pages.
Zinn et al., "In Silico Reconstruction of the Viral Evolutionary Lineage Yields a Potent Gene Therapy Vector," Cell Rep, Aug. 2015, 12(6):1056-1068.
Office Action in Canadian Appln. No. 3174781, dated Oct. 30, 2023, 4 pages.
Office Action in Chinese Appln. No. 202180027825.0, dated Jan. 3, 2024, 15 pages (with English translation).
Xue, "Study on pathogenic mechanism of NMNAT1 mutation, and construction and gene therapy of NMNAT1-LCA9 mouse model," China Doctoral Thesis, Zhejiang University, Jun. 15, 2018, retrieved from the Medicine and Health Science Series of Chinese Doctoral Dissertations Full-text Database, pp. 47 and 77, 6 pages (with English abstract).
Office Action in Chinese Appln. No. 202180027825.0, dated Jun. 21, 2024, 12 pages (with English translation).
Arbabi et al., "Gene therapy for inherited retinal degeneration," Journal of Ocular Pharmacology and Therapeutics, 2019, 35(2):79-97.
Extended European Search Report in European Appln. No. 21767865.5, dated Jul. 11, 2024, 10 pages.
Williams et al., "Vitamin $B_3$ modulates mitochondrial vulnerability and prevents glaucoma in aged mice," Science, Feb. 2017, 355(6326):756-760.
Office Action in Chinese Appln. No. 202180027825.0, mailed on Sep. 29, 2024, 11 pages (with English translation).
Xue, "Characterizations of NMNATI mutants, and the construction of NMNAT1-LCA9 mouse model and gene therapy," China Doctoral Thesis, Zhejiang University, Jun. 15, 2018, retrieved from the Medicine and Health Science Series of Chinese Doctoral Dissertations Full-text Database, 56 pages (with English translation of pp. 6, 47, 71-72, and 77).

\* cited by examiner

Codon optimized *NMNAT1* cDNA

```
1-75     ATGGAAAATTCAGAGAAAACTGAAGTGGTGCTGTTGGCATGTGGATCGTTCAACCCCATCACCAACATGCATCTG
              C     G         T CG T     T A   T                         C C 76-150   CGCCTCTTTGAACTGGCCAAAGACTACATGAATGGAACTGGAAGATACACTGTGGTCAAAGGCATCATCTCCCCA
          A T  G   G      G                   A         A T                   T T 151-225  GTGGGGGATGCATACAAGAAGAAGGGCTTGATCCCTGCCTACCACCGGGTCATCATGGCTGAGCTGGCCACCAAG
             T      C      A AC T      T                     A  T 226-300  AACTCAAAATGGGTGGAAGTGGACACCTGGGAGTCACTGCAAAAGGAGTGGAAGGAAACCCTTAAAGTCCTGCGG
          T T         T A    AAGT  G           A G  G G    AA 301-375  CATCACCAGGAAAAGCTGGAAGCCTCGGACTGTGACCACCAGCAGAACAGCCCCACCCTTGAACGCCCAGGGAGA
          C T A  G  AT  G T A T       T           TCA T  A  AG T A G 376-450  AAGCGCAAGTGGACTGAGACCCAAGACTCAAGCCAGAAGAAGTCGCTGGAACCCAAGACCAAAGCTGTCCCAAAG
          A G        A A     T  A         A C A G A A             G 451-525  GTGAAACTCCTCTGTGGAGCTGACCTCCTGGAATCGTTGCTGTGCCTAATCTCTGGAAGTCGGAAGATATCACC
          C  G G G    G A TT AT  G C      T C T G      AGT    C 526-600  CAAATTGTGGCCAACTATGGCCTGATCTGTGTGACTAGAGCTGGTAATGATGCCCAGAAATTCATCTATGAATCA
           C           G C A    T CG  A       T   G T                         G 601-675  GATGTGCTGTGGAAGCACCGGAGCAACATCCATGTGGTCAATGAGTGGATTGCAAATGACATCTCCTCCACCAAG
                 A          T C    G   A     CT          A    A 676-750  ATCAGAAGGGCCCTGAGGCGGGGACAGTCGATCAGGTACTTGGTCCCAGACCTTGTCCAAGAGTACATTGAAAAG
          C G A   C AA   C   AGC TC C       A         T              A 751-825  CACAACCTCTACAGCTCAGAGTCAGAGGATCGCAATGCAGGAGTGATCCTGGCCCCTCTCCAGCGGAACACTGCA
          T  T G     T  AGT A CAG     T G C               T G AA 826-840  GAGGCCAAGACTTAG
          A  T     A
```

*FIG. 1A*

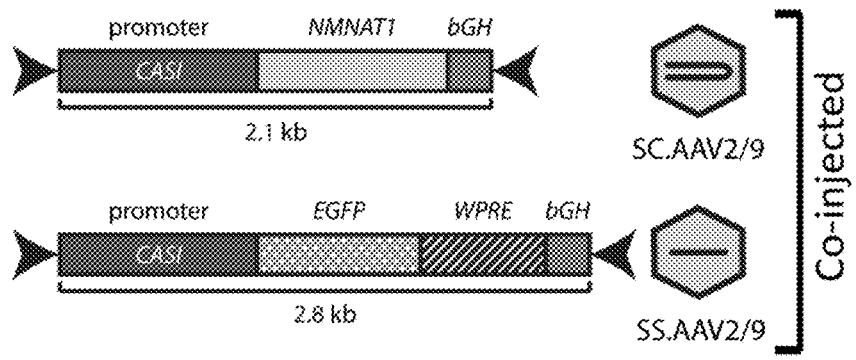
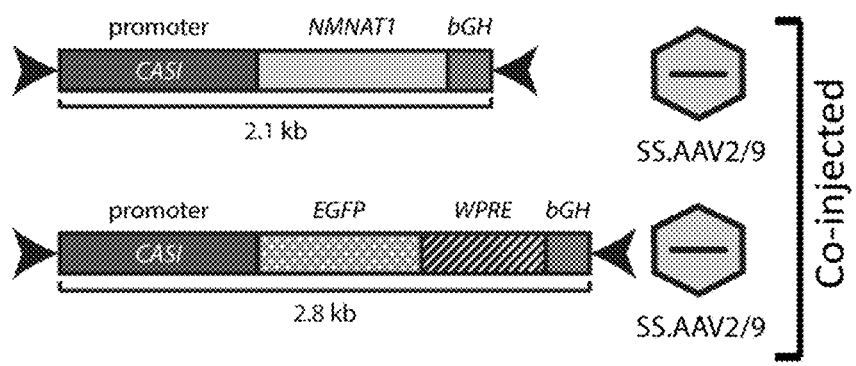
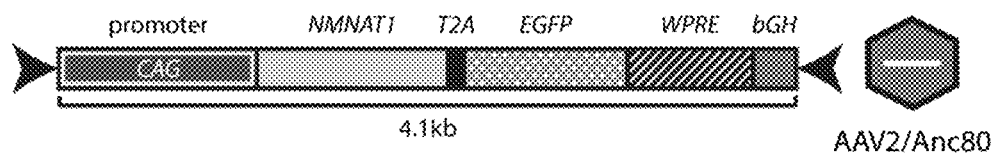
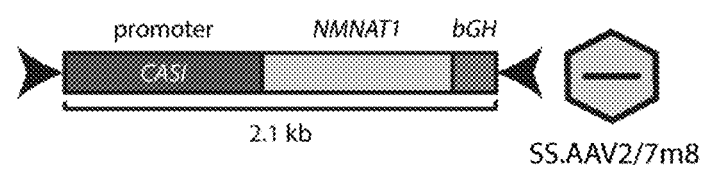
FIGs. 1B-E

FIG. 3A-C

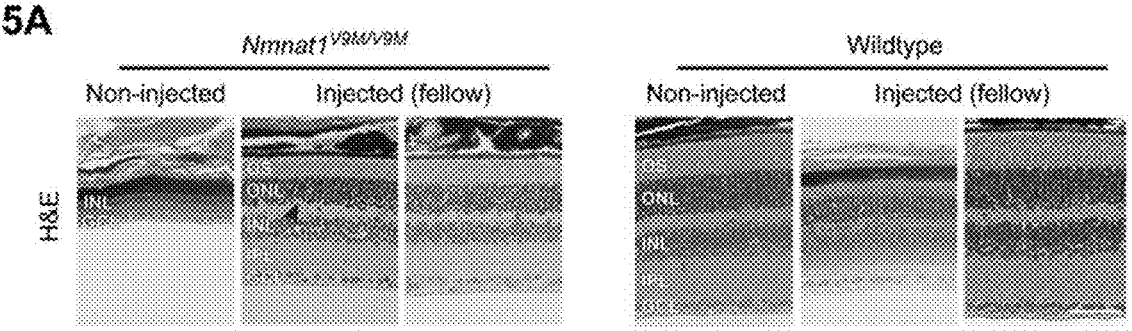
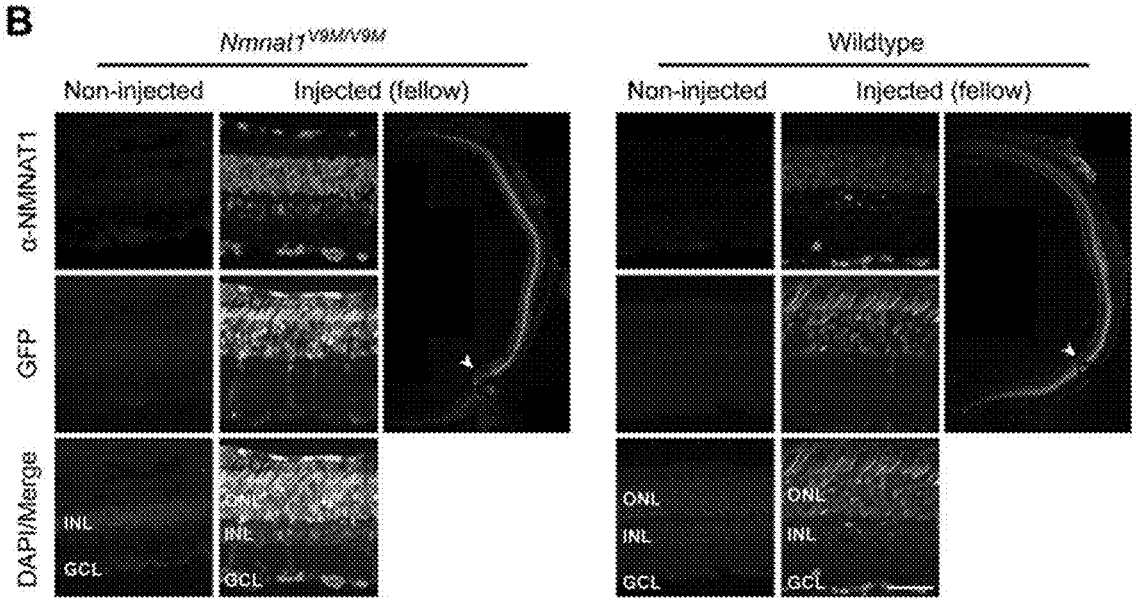
FIGs. 5A-B

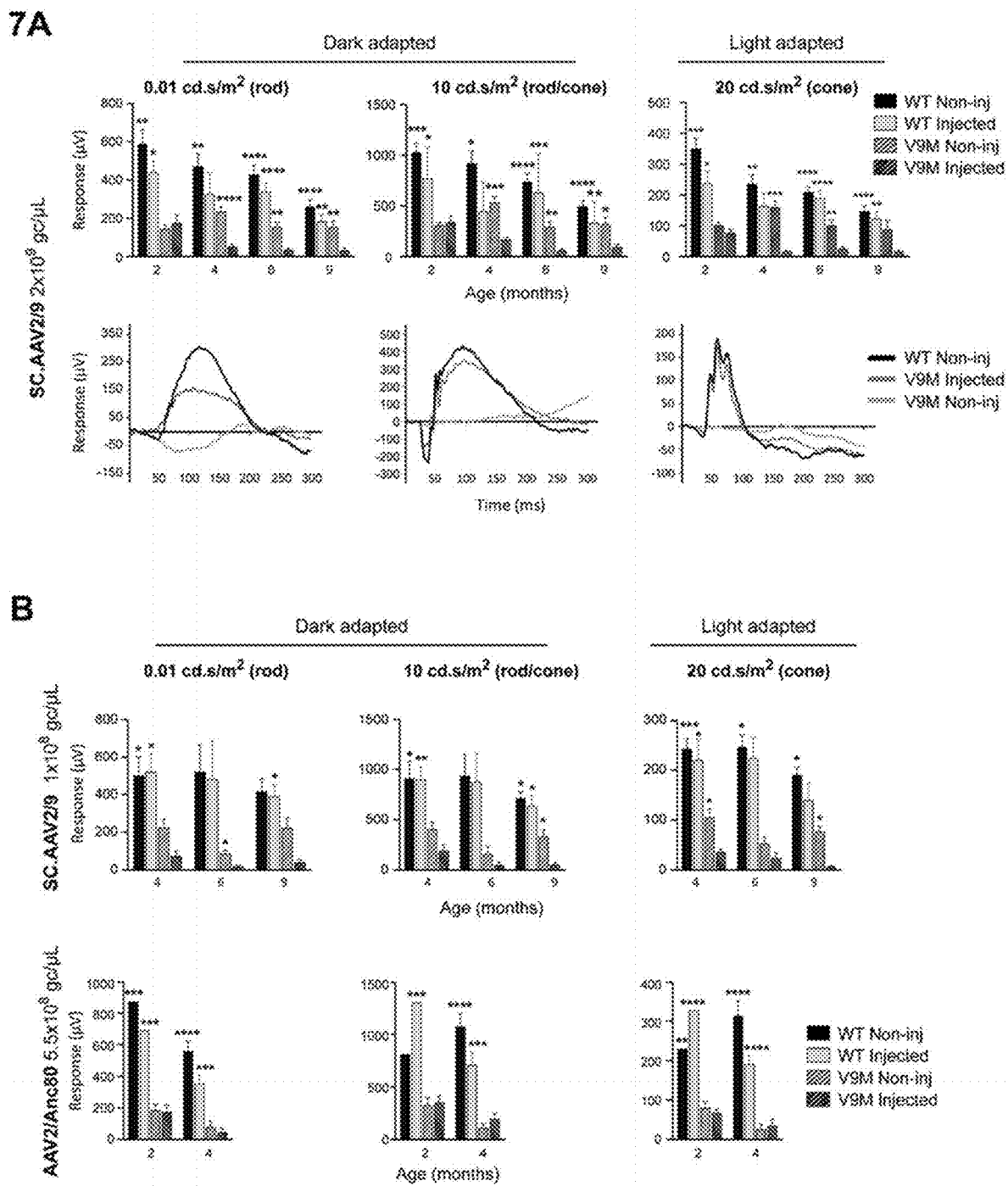
FIGs. 7A-B

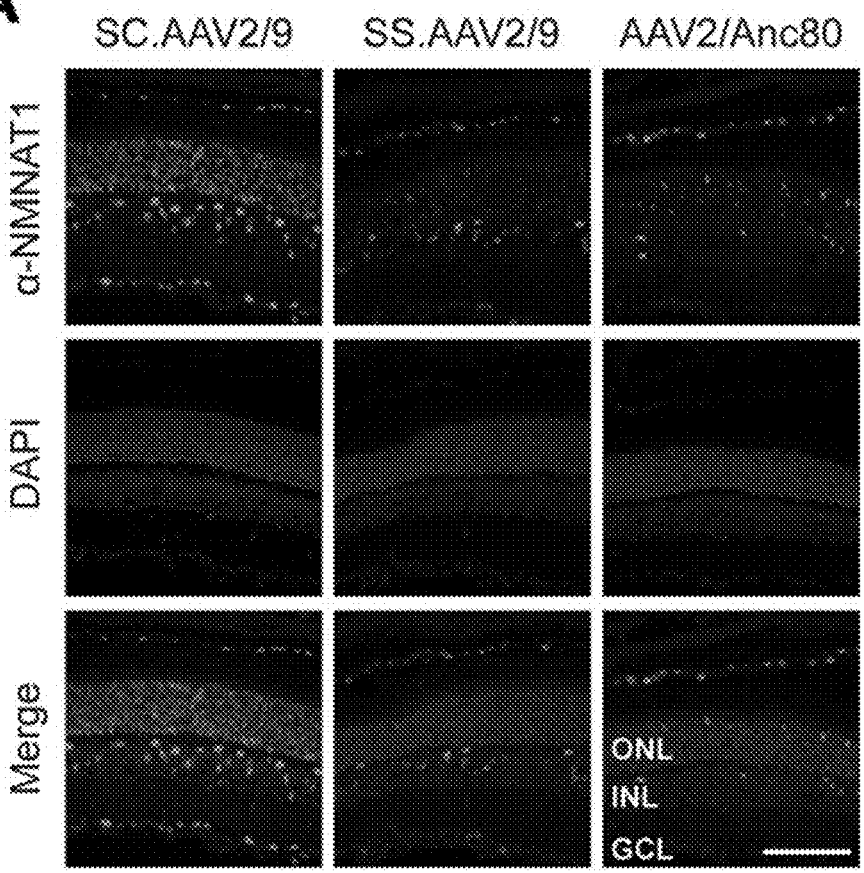
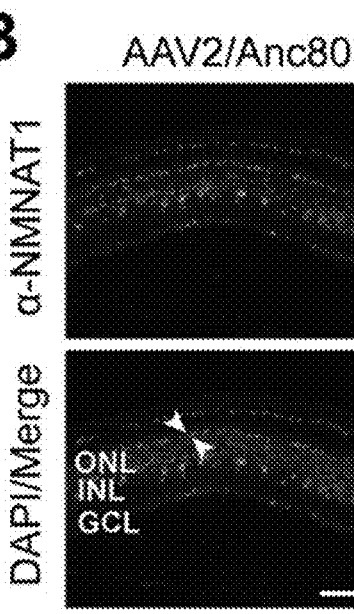
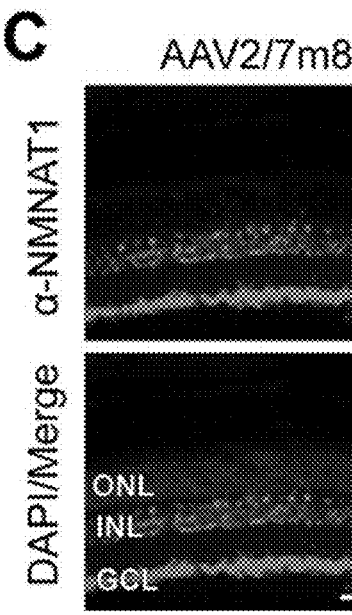
FIGs. 8A-C

GENE THERAPY FOR NMNAT1-ASSOCIATED RETINAL DEGENERATION

CLAIM OF PRIORITY

This application claims the benefit of U.S. Provisional Patent Application Ser. No. 62/988,260, filed on Mar. 11, 2020. The entire contents of the foregoing are hereby incorporated by reference.

FEDERALLY SPONSORED RESEARCH OR DEVELOPMENT

This invention was made with Government support under Grant No. EY012910 awarded by the National Institutes of Health. The Government has certain rights in the invention.

SEQUENCE LISTING

This document includes a sequence listing submitted to the United States Patent and Trademark Office via the electronic filing system as an ASCII text file. The sequence listing, which is incorporated-by-reference herein, is titled "Sequence_Listing.txt," was created on Apr. 9, 2021, and has a size of 6 kilobytes.

TECHNICAL FIELD

The present invention relates to methods and compositions for gene therapy of retinal degeneration related to mutations in nicotinamide mononucleotide adenylyltransferase 1 (NMNAT1).

BACKGROUND

NMNAT1-associated retinal degeneration is an early-onset, recessive disease that causes severe vision loss[1-4] during the first or second decade of life.[5] The affected gene, nicotinamide mononucleotide adenylyltransferase 1 (NMNAT1), encodes a ubiquitously-expressed enzyme that is essential for regenerating $NAD^+$ in cell nuclei.[1,6] The nuclear $NAD^+$ pool is important to many cellular processes, including those related to DNA repair, gene expression, cell signaling, and cell senescence.[7-10] At least thirty-four mutations in NMNAT1 are associated with retinal degeneration,[10,11] each of which is presumed to decrease enzymatic activity to varying degrees.[4] Since inheritance of tabttwo completely nonfunctional alleles is considered embryonic lethal based on studies in Nmnat1 knockout mice, a profound but incomplete loss of nuclear $NAD^+$ likely causes disease.[12] While two other NMNAT isoforms, NMNAT2 and NMNAT3, have the same $NAD^+$ synthase function in the cytosol and mitochondria, respectively,[8,13] it is apparent that neither can compensate for the loss of NMNAT1,[12] at least in the retina. The isolated nature of this disease can be explained partially by the recent finding that neural retinas of Nmnat1$^{V9M/V9M}$ mice, the same model used in the present study, have decreased levels of $NAD^+$ (accompanied by increased levels of the precursor), whereas levels in other tissues, including brain tissue, remain unchanged (Greenwald et al., RD2018 abstract). However, the underlying reason that the retina has this unique vulnerability remains unclear.

SUMMARY

Provided herein are methods for treating retinal degeneration caused by mutations in a nicotinamide mononucleotide adenylyltransferase 1 (NMNAT1) gene in a human subject. In general, the methods include delivering to the eye of the subject a therapeutically effective amount of an Adeno-associated virus (AAV) vector comprising a sequence encoding human NMNAT1 (e.g., at least 80, 85, 90, 95, 97, 98, or 99% identical to a human NMNAT1 protein of SEQ ID NO:3), operably linked to a promoter that drives expression in retinal cells, preferably in photoreceptors.

In some embodiments, the promoter is a CAG, CASI, CMV, RHO, or rhodopsin kinase (GRK1) promotor.

In some embodiments, the NMNAT1-encoding sequence is at least 80% identical to a wild type (SEQ ID NO:2) or codon optimized (SEQ ID NO:1) sequence.

In some embodiments, the vector is delivered via sub-retinal injection.

Also provided herein are methods for increasing expression of NMNAT1 in the eye of a human subject. The methods include delivering to the eye of the subject a therapeutically effective amount of an Adeno-associated virus type 2 (AAV2) vector comprising a sequence encoding human NMNAT1, operably linked to a promoter that drives expression in the retina, preferably in photoreceptor cells.

In some embodiments, the promoter is a CAG, CASI, CMV, RHO, or rhodopsin kinase (GRK1) promotor.

In some embodiments, the NMNAT1 sequence is codon optimized.

In some embodiments, the vector is delivered via sub-retinal injection.

Also provided herein is an Adeno-associated virus type 2 (AAV2) vector comprising a sequence encoding human NMNAT1, operably linked to a promotor that drives expression in the retina, preferably in the photoreceptor cells.

In some embodiments, the promotor is a CAG, CASI, CMV, RHO, or rhodopsin kinase (GRK1) promotor.

In some embodiments, the NMNAT1 sequence is codon optimized. In some embodiments, the NMNAT1-encoding sequence is at least 80% identical to a wild type (SEQ ID NO:2) or codon optimized (SEQ ID NO:1) sequence.

Also provided are pharmaceutical compositions comprising the vectors described herein, formulated for delivery via sub-retinal injection.

The vectors and compositions described herein can be used, e.g., in treating retinal degeneration caused by mutations in NMNAT1 in the eye of a human subject and/or in increasing expression of NMNAT1 in the eye of a human subject.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DESCRIPTION OF DRAWINGS

FIGS. 1A-E. NMNAT1 transgene sequence and viral reagents. A) The 840-nucleotide codon-optimized human NMNAT1 cDNA sequence (black text, SEQ ID NO: 1) has 174 silent substitutions (bolded), and the identities of the respective wildtype nucleotides are shown beneath (the WT sequence is presented as SEQ ID NO:2 herein). B) NMNAT1, driven by the CASI promoter and packaged into SC.AAV2/9, is co-delivered into mice with an EGFP reporter construct that is driven by the same promoter, followed by WPRE, and packaged in SS.AAV2/9. C) Identical to Panel A, except that both constructs are packaged in SS.AAV2/9.

D) A self-cleaving NMNAT1-EGFP fusion construct, driven by the CAG promoter and followed by WPRE, is packaged in the AAV2/Anc80 vector. E) NMNAT1, driven by the CASI promoter and packaged into SS.AAV7m8. Abbreviations: bGH, bovine growth hormone polyadenylation signal; EGFP, enhanced green fluorescent protein; WPRE, woodchuck hepatitis virus posttranslational regulatory element; T2A, thosea asigna virus 2A self-cleaving sequence.

Figure 2:
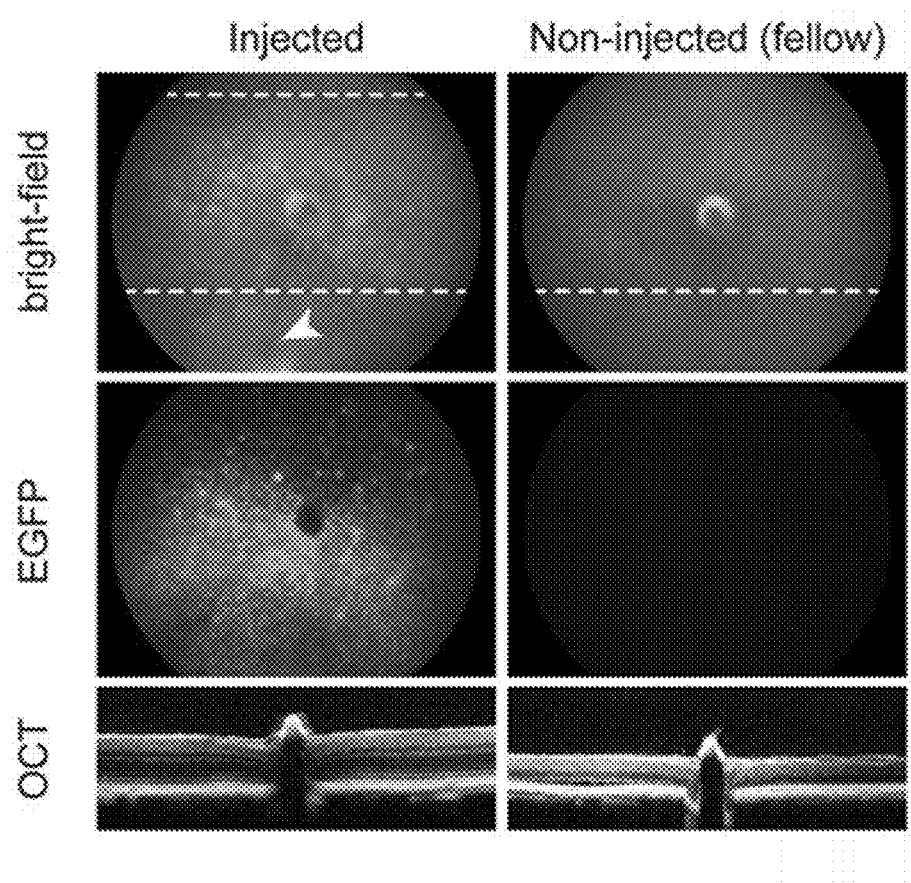

FIG. 2. In vivo imaging. Bright-field fundus images of an injected (left column) and non-injected (right column) retina from a four-month-old $Nmnat1^{V9M/V9M}$ mouse show the planes for photoreceptor layer measurements in OCT images. White dashed lines: inferior retina (proximal to injection site of injected retina); dashed line: superior retina (distal to injection site of injected eye); arrowhead indicates the injection site (top row). EGFP is visible only in the injected retina (middle row). Representative cross-sectional OCT images showing that the retina injected with the SC.AAV2/9 reagent at $2 \times 10^9$ gc/µL (left) is thicker than the non-injected retina (right).

Figure 3:
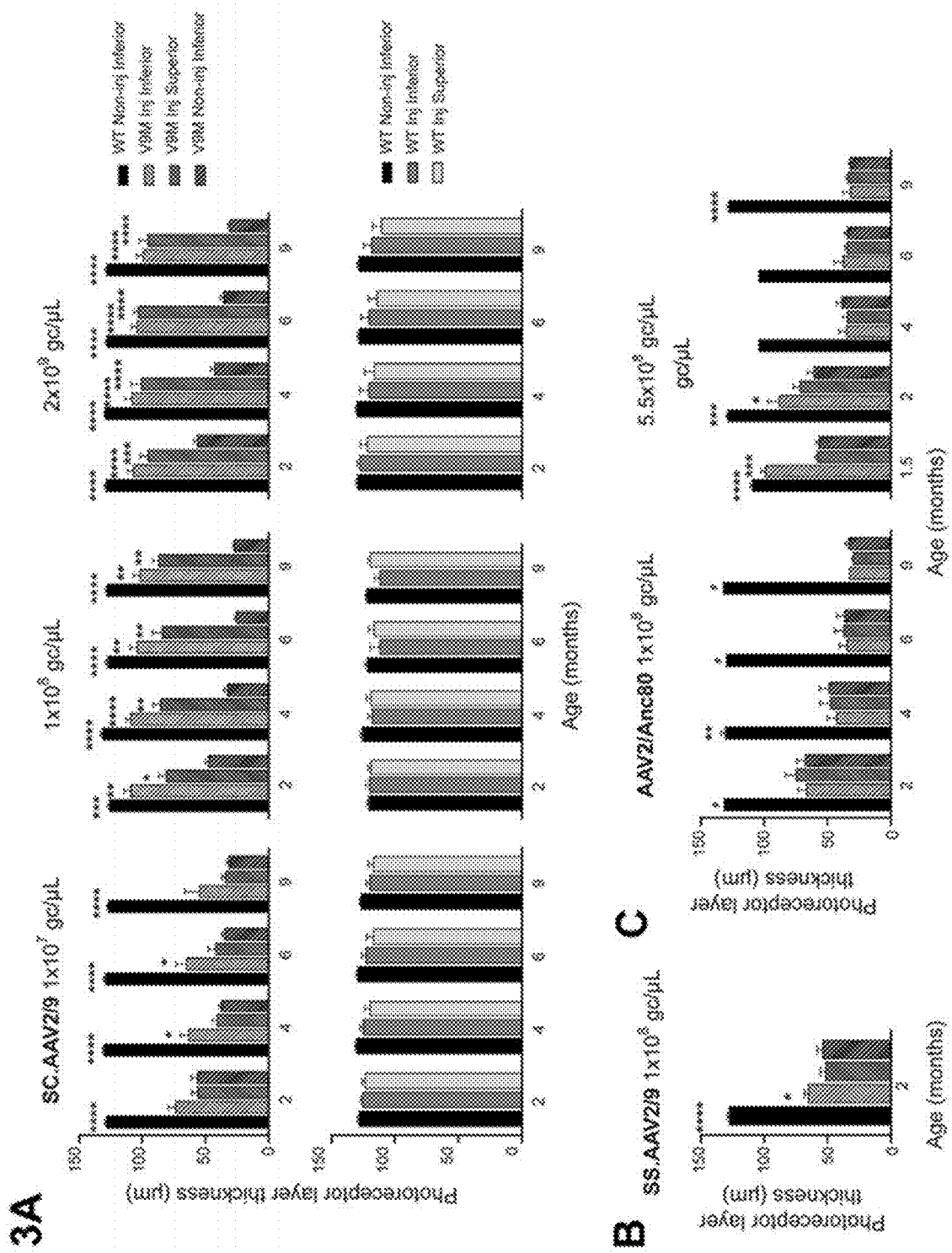

FIGS. 3A-C. In vivo imaging shows the SC.AAV2/9 reagent provides stable structural rescue of the retina. A) Photoreceptor layer thickness measurements from OCT images across nine months of age following injection with the SC.AAV2/9 reagent at $1 \times 10^7$ gc/µL, $1 \times 10^8$ gc/µL, and $2 \times 10^9$ gc/µL show rescue at higher doses. Comparisons of the inferior region of non-injected $Nmnat1^{V9M/V9M}$ retinas with the inferior and superior regions of the fellow injected retinas and the inferior region of non-injected wildtype littermate control retinas (top row). Photoreceptor layer thickness measurements of the inferior region of non-injected wildtype retinas compared with the superior and inferior regions of the injected fellow retinas indicate minimal toxicity of the reagent (bottom row). B) Photoreceptor layer thickness measurements show no detectable rescue by SS.AAV2/9 reagent at $1 \times 10^8$ gc/µL at age two months. C) Photoreceptor layer thickness measurements showed no detectable rescue by AAV2/7m8 reagent at $3 \times 10^8$ gc/µL at age two months, but photoreceptor layer thickness measurements showed transient rescue using AAV2/Anc80 at $5.5 \times 10^8$ gc/µL across four months of age. Error bars represent the S.E.M.; * p<0.05,  p<0.1, p<0.001, ** p<0.0001.

Figure 4:
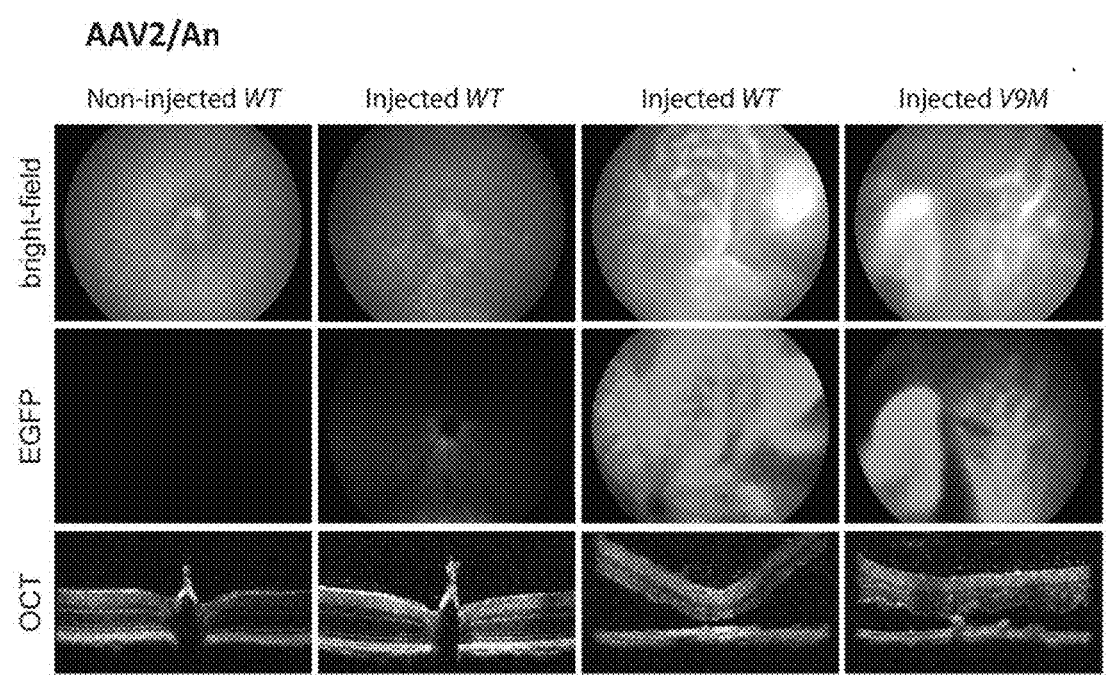

FIG. 4. High titer Anc80/Anc80 reagent is toxic to retina. In contrast to non-injected wildtype mice (first column) and mice injected with the $5.5 \times 10^8$ gc/µL dose (second column), bright-field fundus images (top row) of injected wildtype retina (third column) and injected $Nmnat1^{V9M/V9M}$ retina (fourth column) shows wrinkling of retina and hemorrhage e). Cell transduction in injected retinas was confirmed by EGFP expression (middle row). In the injected mice, OCT images (bottom row) show retinal detachment, disruption of the neural retina, and intravitreal cellular infiltrates (visible as hyper-reflective puncta immediately above neural retina). Mice imaged at age six weeks.

FIGS. 5A-B. Ex vivo imaging shows structural rescue at cellular level in retina of treated with the SC.AAV2/9 reagent. Images of nine-month-old $Nmnat1^{V9M/V9M}$ and wildtype retina are shown in the left and right panel groups, respectively. A) H&E staining of non-injected (left panel) and injected (middle and right panels) retinas. Middle and right panels show morphological variability associated with injection (more damage, middle panel; less damage, right panel) within the primary region of transduction. Black arrowhead indicates mild scalloping of the ONL. 40×mag, scale bar 75 µm. B) Non-injected retina (left column, both panel groups) shows neither α-NMNAT1 antibody reactivity nor EGFP expression whereas the injected fellow retinas show both (center column, both panels). DAPI is the counterstain zn merged images. Montages showing the entirety of each retina section are labeled with the α-NMNAT1 antibody and counterstained with DAPI (right panel of left and right panel groups) to show the extent of transgene expression across the retina. White arrowheads indicate the injection site. 63× magnification, scale bar 50 µm.

Figure 6:
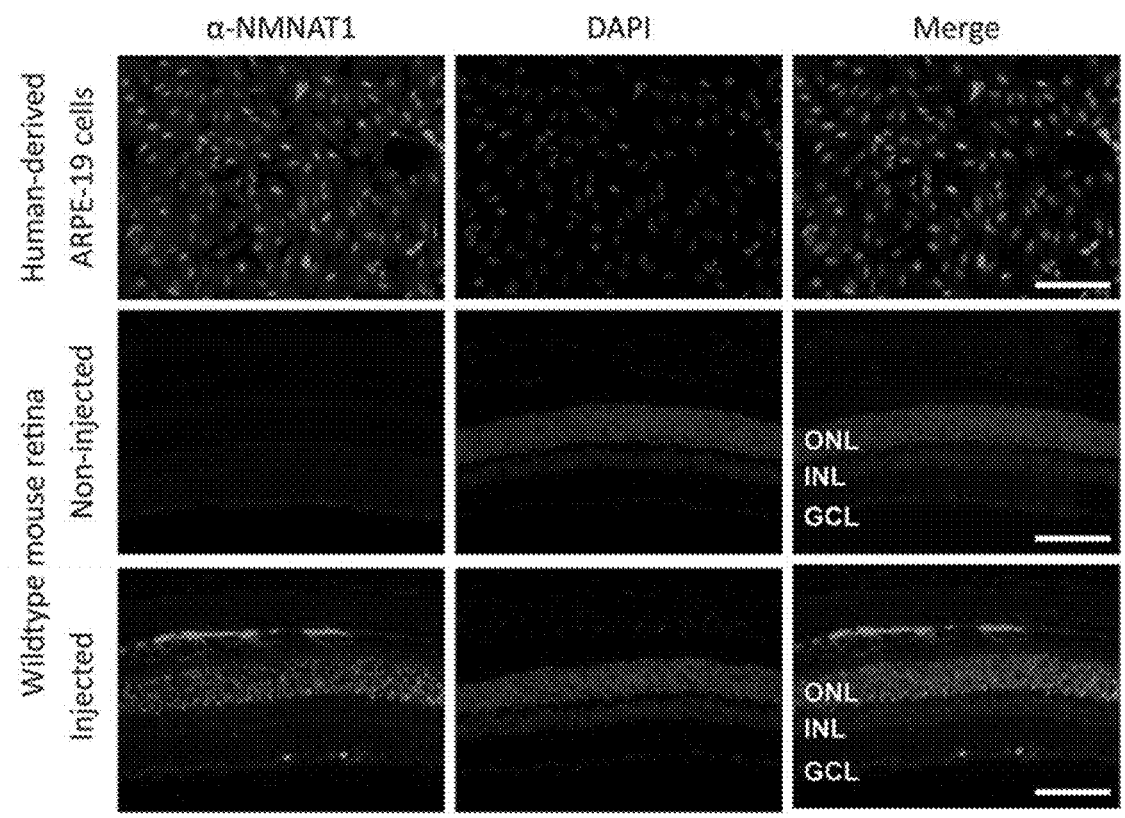

FIG. 6. Validation of anti-human NMNAT1 polyclonal antibody. In human-derived ARPE-19 cells (top row), α-NMNAT1 labeling (left column) and DAPI stained cell nuclei (center column) co-localized (right column). Wildtype mouse retina showed minimal cross-reactivity with endogenous mouse NMNAT1 (middle row). In mouse retina expressing human NMNAT1 following injection with AAV, immunoreactivity was detected in cell nuclei (bottom row). Magnification 20×; scale bars: 100 µm.

FIGS. 7A-B. ERG shows preservation of retinal function by treatment with SC.AAV2/9 reagent. A) Retinas from $Nmnat1^{V9M/B9M}$ mice treated with a $2 \times 10^9$ gc/µL dose of SC.AAV2/9 generate significantly larger rod, mixed rod/cone, and cone-isolating ERGs than the untreated fellow retinas, as measured by the ERG b-wave. Measurements from the non-injected $Nmnat1^{V9M/V9M}$ retinas are compared to injected fellow retinas and to non-injected and injected retinas of wildtype mice (top row). Representative ERG waveforms from a six-month-old treated $Nmnat1^{V9M/V9M}$ mouse (treated retina, gray trace; untreated retina, light gray trace) and an age-matched wildtype littermate (black trace) (bottom row). B) ERG measurements to nine months of age for mice injected with SC.AAV2/9 at a dose of $1 \times 10^8$ gc/µL show a weaker level of rescue than for the $2 \times 10^9$ gc/µL dose (top row), and ERG measurements to 4 months of age with AAV2/Anc80 at a dose of $5.5 \times 10^8$ gc/µL indicate no efficacy (bottom row). Error bars represent the S.E.M.; * p<0.05,  p<0.1, * p<0.001, **** p<0.0001.

FIGS. 8A-C. Early transgene expression in photoreceptors is required for a successful therapy. A) At 14 days post-injection, dense α-NMNAT1 immunoreactivity was observed in the retina (notably in the ONL) injected with the SC.AAV2/9 reagent (left column), whereas this signal was sparse in age-matched retinas injected with either the SS.AAV2/9 (center column) or the AA2/Anc80 (right column) reagent. 40× magnification, scale bar 75 µm. B) Representative retina from a 5.5-week-old wildtype mouse was injected with AAV2/Anc80 at p1, shows strong α-NMNAT1 immunoreactivity in virtually all cell types except for rod photoreceptors. The top row of labeled cells in the ONL are cones (between arrowhead), and DAPI is the counterstain. 20× magnification, scale bar represents 100 µm. C). Intravitreal injection at age two weeks of AAV2/7m8 ($3 \times 10^8$ gc/µL) in a control mouse generates strong NMNAT1 expression in the INL and GCL but not in the ONL at four weeks post-injection. DAPI is the counterstain; 20× magnification, scale bar 100 µm.

DETAILED DESCRIPTION

Currently, no treatment exists for NMNAT1-associated retinal degeneration. Because patients incur considerable vision loss during the first years of life, but are expected to have normal longevity, an early intervention has the potential to preserve sight for many decades. Since this disease has a recessive inheritance pattern[10] and because NMNAT1 is a relatively small gene,[14] treatment with adeno-associated virus (AAV)-mediated gene augmentation therapy is an attractive strategy. At 840 bp, human NMNAT1 cDNA is well within the ~4.7 kb maximum cargo capacity for single-stranded AAV (SS.AAV)[15] and the ~2.2 kb maximum cargo capacity of self-complementary AAV (SC.AAV).[16] This approach of supplementing cells with a normal copy of a mutant gene via an AAV vector to maintain retinal cell viability is presently being used as an FDA approved therapy (Luxturna) in patients for the treatment of RPE65-associated retinal degeneration.[17] In addition, there are ongoing clinical trials of AAV-mediated gene augmentation therapies for choroideremia,[18] achromatopsia (clinicaltrials.gov, accessed Nov. 7, 2019), MERTK-retinitis pigmentosa,[19] X-linked retinitis pigmentosa (recruiting, clinicaltrials.gov, accessed Nov. 7, 2019), and X-linked retinoschesis,[20] among others,[15] as well as numerous preclinical studies for other inherited retinal degenerations.[21-24]

When NMNAT1 was first reported as a disease gene in 2012, a suitable animal model was not available for evaluating potential therapies in situ. Traditional Nmnat1 knock-out mice were not viable[12] and conditional knockout animals, which ablate Nmnat1 in targeted retinal cells, would not have accurately represented the physiology of the disease. We recently reported the characterization of an NMNAT1-associated retinal disease mouse model that is homozygous for the p. Val9Met (V9M) mutation in Nmnat1,[1,25] an allele that has been found to cause retinal disease in members of unrelated families.[4,10] The founder of this mouse line was identified during an ENU mutagenesis screen. The homozygous mutant progeny (Nmnat1$^{V9M/V9M}$) invariably develop an early-onset isolated retinal disease without obvious detriments to longevity, mobility, or cognition, much like the humans they model. Nmnat1$^{V9M/V9M}$ mice have fully mature retinas and reliable responses to light, as detected by the electroretinogram (ERG), at three weeks of age, but a week later, the photoreceptor layer shows signs of degeneration accompanied by reduced function. By approximately four months of age, the retina is severely degenerated, and responses to light are often undetectable.[25] Given that the mutation in this mouse is present in the patient population and there is an opportunity for intervention during the first month of life, this model is appropriate for testing therapies that aim to protect the retina from NMNAT1-associated disease.

For the purpose of developing a therapy to preserve vision in people with Nmnat1-associated retinal degeneration, we used the p. V9M-Nmnat1 mouse model to test the hypothesis that providing retinal cells with a normal copy of NMNAT1 prevents disease progression. To accomplish this, a human NMNAT1 cDNA was delivered to the retinas of Nmnat1$^{V9M/V9M}$ mice via several recombinant AAV2 vectors that were evaluated independently. Efficacy varied across viral preparations and experimental conditions, and therefore, we aimed to understand why specific variables were associated with success or failure and how these lessons might generalize to assist in the development of other AAV-mediated gene therapies.

Morphological and functional data collected from Nmnat1$^{V9M/V9M}$ mice treated using AAV-mediated gene augmentation offer the first demonstration of any type of therapy that targets NMNAT1-associated retinal degeneration. Because of the narrow therapeutic window in this mouse model, a self-complementary viral vector was required so that the transgene would be expressed early enough to rescue vulnerable cells. A self-complementary AAV differs from a single-stranded vector in that it contains an inverted repeat genome that folds to make double-stranded DNA.[42] In this way, the virus is able to bypass the rate-limiting step of second strand DNA synthesis that is normally required prior to transgene expression,[31,43] as well as circumvent the vector genome instability that briefly follows DNA replication.[44] Also, self-complementary vectors require neither transport to the nucleus nor uncoating from the capsid prior to transgene expression.[16] In this model, single-stranded vectors, including one that was the same AAV serotype/capsid (AAV2/9) and contained the identical genomic cargo, yielded unfavorable results; however, such single stranded vectors may be of use in other species including humans.

The therapeutic window of the Nmnat1$^{V9M/V9M}$ mouse was bounded by the limitation of rod photoreceptor developmental biology[45] on the early side and by the onset of degeneration at slightly under four weeks of age on the late side.[25] Logically, the earliest possible intervention would be preferred, implying treatment immediately after birth. However, the observation that rods do not show strong transgene expression following neonatal injections agrees with recent reports by other groups describing that developing rod photoreceptors in P0-P1 mice are not competent to be transduced by AAV.[45,46] The need for transgene expression in photoreceptors was made clear by the experiment in which intravitreal injections of AAV2/7m8 were delivered to two-week-old mice. This treatment provided no therapeutic benefit despite strong and widespread coverage of the inner retinal cell layers. Using self-complementary AAV5, Petit et al. reported that approximately twice as many rods become transduced if the injection is provided at P21 rather than P10.[45]

However, since SC.AAV2/9 requires longer than one week to express NMNAT1 in the mouse retina, delaying the intervention until P21 would have allowed uncontested disease progression during the viral incubation period. Instead, injections were performed at ~P16, which afforded the time necessary for transgene expression to be initiated while still having the possibility of transducing a substantial portion of the rod population. In this case, the number of photoreceptors that were rescued by the treatment was sufficient to maintain ~80% of ONL thickness in comparison to age-matched wildtype littermates. It should be noted that while this preservation of retinal structure was immediate, rescue of function was not apparent by ERG until 3.5 months post-injection.

In the present methods, delivery is performed during the therapeutic window in human patients. Rescued retinas in Nmnat1$^{V9M/V9M}$ mice showed preservation of cone and rod photoreceptor function that was stable for months. While ERGs from eyes treated with SC.AAV2/9 were approximately fifty percent of what was measured in non-injected wildtype retinas, this difference is consistent with prior observations that subretinal injections dampen the ERG response, likely due to mechanical damage sustained during the surgical procedure.[50] This possibility is supported by the finding that the injected retinas of the wildtype littermates also tended to have b-wave amplitude decrements, although typically less extensive, and regions in which the photoreceptor layer was thinner following injection. In addition, photoreceptor degeneration that appears to have occurred during the viral incubation period may have also contributed to the lower signal. An alternative hypothesis is that some cells were augmented such that they overexpressed NMNAT1 and that this is not compatible with viability. However, the reason for such a ceiling effect on the therapeutic index for NMNAT1/NAD$^+$ supplementation is not obvious. In the mutant mice, the highest dose ($2\times10^9$ gc/µL) of the reagent produced the best outcome, but due to manufacturing constraints, it was not possible to test the effects of even higher levels.

The present methods can use ubiquitously activating promoters or cell type-specific promoters. Characterization of the p. V9M-Nmnat1 mouse model indicated that photoreceptors were the first cells to be affected by the disease, followed by inner retinal cells and the RPE,[25] and we know from experiments described here that the photoreceptors must be treated if the retina is to be preserved. Thus in some methods a photoreceptor-specific promoter is used to provide rescue of the retina. However, other cell types may degenerate at slower rates in response to low nuclear NAD", causing a secondary degeneration that cannot be mitigated by treating only photoreceptors. In that case, ganglion cell, bipolar, and Müller glia-specific promoters could then be used.

As shown herein, the exemplary SC.AAV2/9 reagent with CASI driving NMNAT1 expression demonstrated success use of gene augmentation therapy in patients with NMNAT1-associated retinal degeneration. In some embodiments, rapidly driving the initiation of transgene expression with a self-complementary vector is an optimal strategy.

This therapy has the potential to provide many decades of vision to people worldwide who would otherwise sustain severe vision loss early in life.

Vectors

Described herein are targeted expression vectors for in vivo transfection and expression of a polynucleotide that encodes a NMNAT1 polypeptide as described herein, in the retina, e.g., in photoreceptors, e.g., primarily or only in photoreceptors. In some embodiments the expression is also in inner retinal cells or RPE cells. Expression constructs of such components can be administered in any effective carrier, e.g., any formulation or composition capable of effectively delivering the component gene to cells in vivo. Approaches include insertion of the gene in viral vectors, including recombinant retroviruses, adenovirus, adeno-associated virus, lentivirus, and herpes simplex virus-1, alphavirus, vaccinia virus, or recombinant bacterial or eukaryotic plasmids; preferred viral vectors are adeno-associated virus type 2 (AAV2). Viral vectors transfect cells directly; plasmid DNA can be delivered naked or with the help of, for example, cationic liposomes (lipofectamine) or derivatized (e.g., antibody conjugated), cationic dendrimers, inorganic vectors (e.g., iron oxide magnetofection), lipidoids, cell-penetrating peptides, cyclodextrin polymer (CDP), polylysine conjugates, gramacidin S, artificial viral envelopes or other such intracellular carriers, as well as direct injection of the gene construct or CaPO4 precipitation carried out in vivo.

An exemplary approach for in vivo introduction of nucleic acid into a cell is by use of a viral vector containing nucleic acid, e.g., a cDNA. Infection of cells with a viral vector has the advantage that a large proportion of the targeted cells can receive the nucleic acid. Additionally, molecules encoded within the viral vector, e.g., by a cDNA contained in the viral vector, are expressed efficiently in cells that have taken up viral vector nucleic acid.

Viral vectors can be used as a recombinant gene delivery system for the transfer of exogenous genes in vivo, particularly into humans. These vectors provide efficient delivery of genes into cells, and in some cases the transferred nucleic acids are stably integrated into the chromosomal DNA of the host. Protocols for producing recombinant viruses and for infecting cells in vitro or in vivo with such viruses can be found in Ausubel, et al., eds., *Gene Therapy Protocols Volume 1: Production and In Vivo Applications of Gene Transfer Vectors*, Humana Press, (2008), pp. 1-32 and other standard laboratory manuals.

A preferred viral vector system useful for delivery of nucleic acids is the adeno-associated virus (AAV). Adeno-associated virus is a naturally occurring defective virus that requires another virus, such as an adenovirus or a herpes virus, as a helper virus for efficient replication and a productive life cycle. (For a review see Muzyczka et al., Curr. Topics in Micro and Immunol. 158:97-129 (1992); see also Domenger and Grimm, Human Molecular Genetics, 28 (R1): R3-R14 (October 2019)). AAV vectors efficiently transduce various cell types and can produce long-term expression of transgenes in vivo. Although AAV vector genomes can persist within cells as episomes, vector integration has been observed (see for example Deyle and Russell, Curr Opin Mol Ther. 2009 August; 11 (4): 442-447; Asokan et al., Mol Ther. 2012 April; 20 (4): 699-708; Flotte et al., Am. J. Respir. Cell. Mol. Biol. 7:349-356 (1992); Samulski et al., J. Virol. 63:3822-3828 (1989); and Mclaughlin et al., J. Virol. 62:1963-1973 (1989)). AAV vectors, particularly AAV2, have been extensively used for gene augmentation or replacement and have shown therapeutic efficacy in a range of animal models as well as in the clinic; see, e.g., Mingozzi and High, Nature Reviews Genetics 12, 341-355 (2011); Deyle and Russell, Curr Opin Mol Ther. 2009 August; 11 (4): 442-447; Asokan et al., Mol Ther. 2012 April; 20 (4): 699-708. AAV vectors containing as little as 300 base pairs of AAV can be packaged and can produce recombinant protein expression. Space for exogenous DNA is limited to about 4.5 kb. For example, an AAV1, 2, 4, 5, or 8 vector can be used to introduce DNA into the retina, e.g., into photoreceptors, inner retinal cells, or RPE cells (such as those described in Maguire et al. (2008). Safety and efficacy of gene transfer for Leber's congenital amaurosis. N Engl J Med 358:2240-2248. Maguire et al. (2009). Age-dependent effects of RPE65 gene therapy for Leber's congenital amaurosis: a phase 1 dose-escalation trial. Lancet 374:1597-1605; Bainbridge et al. (2008). Effect of gene therapy on visual function in Leber's congenital amaurosis. N Engl J Med 358:2231-2239; Hauswirth et al. (2008). Treatment of leber congenital amaurosis due to RPE65 mutations by ocular subretinal injection of adeno-associated virus gene vector: short-term results of a phase I trial. Hum Gene Ther 19:979-990; Cideciyan et al. (2008). Human gene therapy for RPE65 isomerase deficiency activates the retinoid cycle of vision but with slow rod kinetics. Proc Natl Acad Sci USA 105:15112-15117. Cideciyan et al. (2009). Vision 1 year after gene therapy for Leber's congenital amaurosis. N Engl J Med 361:725-727; Simonelli et al. (2010). Gene therapy for Leber's congenital amaurosis is safe and effective through 1.5 years after vector administration. Mol Ther 18:643-650; Acland, et al. (2005). Long-term restoration of rod and cone vision by single dose rAAV-mediated gene transfer to the retina in a canine model of childhood blindness. Mol Ther 12:1072-1082; Le Meur et al. (2007). Restoration of vision in RPE65-deficient Briard dogs using an AAV serotype 4 vector that specifically targets the retinal pigmented epithelium. Gene Ther 14:292-303; Stieger et al. (2008). Subretinal delivery of recombinant AAV serotype 8 vector in dogs results in gene transfer to neurons in the brain. Mol Ther 16:916-923; and Vandenberghe et al. (2011). Dosage thresholds for AAV2 and AAV8 photoreceptor gene therapy in monkey. Sci Transl Med 3: 88ra54). In some embodiments, the AAV vector can include (or include a sequence encoding) an AAV capsid polypeptide described in WO 2015054653; for example, a virus particle comprising an AAV capsid polypeptide having an amino acid sequence selected from the group consisting of SEQ ID NOs: 1, 3, 5, 7, 9, 11, 13, 15, and 17 of WO 2015054653, and a NMNAT1-encoding sequence as described herein. In some embodiments, the AAV capsid polypeptide is as shown in Table 1 of WO 2015054653, reproduced here:

| Node | Polypeptide (SEQ ID NO) | Nucleic Acid (SEQ ID NO) |
|---|---|---|
| Anc80 | 1 | 2 |
| Anc81 | 3 | 4 |
| Anc82 | 5 | 6 |
| Anc83 | 7 | 8 |
| Anc84 | 9 | 10 |
| Anc94 | 11 | 12 |
| Anc113 | 13 | 14 |
| Anc126 | 15 | 16 |
| Anc127 | 17 | 18 |

In some embodiments, the AAV capsid polypeptide is an Anc80 polypeptide, e.g., an exemplary polypeptide shown in SEQ ID NO: 19 (Anc80L27); SEQ ID NO: 20 (Anc80L59); SEQ ID NO: 21 (Anc80L60); SEQ ID NO: 22 (Anc80L62); SEQ ID NO: 23 (Anc80L65); SEQ ID NO: 24 (Anc80L33); SEQ ID NO: 25 (Anc80L36); and SEQ ID NO: 26 (Anc80L44).

A variety of nucleic acids have been introduced into different cell types using AAV vectors (see for example the references cited above and those cited in Asokan et al., Molecular Therapy (2012); 20 4, 699-708; and Hermonat et al., Proc. Natl. Acad. Sci. USA 81:6466-6470 (1984); Tratschin et al., Mol. Cell. Biol. 4:2072-2081 (1985); Wondisford et al., Mol. Endocrinol. 2:32-39 (1988); Tratschin et al., J. Virol. 51:611-619 (1984); and Flotte et al., J. Biol. Chem. 268:3781-3790 (1993).

In some embodiments, a self-complementary AAV is used, which contains an inverted repeat genome that folds to make double-stranded DNA.

In some embodiments, a gene encoding NMNAT1 is entrapped in liposomes bearing positive charges on their surface (e.g., lipofectins), which can be tagged with antibodies against cell surface antigens of the target tissue (Mizuno et al., No Shinkei Geka 20:547-551 (1992); PCT publication WO91/06309; Japanese patent application 1047381; and European patent publication EP-A-43075).

The vectors can also include promoters, enhancers (e.g., CMV enhancer), other cis-regulatory elements, and/or capsid serotype variants. With regard to promoters, vectors can include promoters that drive expression in many cell types (e.g., CAG, CMV, or CASI) and photoreceptor cells (RHO, rhodopsin kinase (GRK1) and cone arrestin (CAR)) or RPE cells (e.g., promotors for RPE-specific proteins such as VMD2, RPE65, RLBP1, RGR, or TIMP3) (Esumi et al., Journal Biological Chemistry. 2004; 279:19064-73; Guziewicz et al., PLOS One. 2013; 8: e75666; Allocca et al., J Virol. 2007; 81:11372-80; see also Domenger and Grimm, Human Molecular Genetics, 28 (R1): R3-R14 (October 2019)). Synthetic promoters ProC1 and ProDS could also be used, see, e.g., Jüttner et al. Nat Neurosci. 2019 August; 22 (8): 1345-1356. Other cis-regulatory elements can include woodchuck hepatitis virus post-transcriptional regulatory element (WPRE) or minute virus of mice (MVM) intron (see Domenger and Grimm, Human Molecular Genetics, 28 (R1): R3-R14 (October 2019)).

The pharmaceutical preparation of the gene therapy construct can consist essentially of the gene delivery system (viral vector and any associated agents such as helper viruses, proteins, lipids, and so on) in an acceptable diluent, or can comprise a slow release matrix in which the gene delivery vehicle is embedded. Alternatively, where the complete gene delivery system can be produced intact from recombinant cells, e.g., retroviral vectors, the pharmaceutical preparation can comprise one or more cells, which produce the gene delivery system.

Sequences

The present methods include delivery of sequences encoding human NMNAT1. Exemplary human nicotinamide nucleotide adenylyltransferase 1 (NMNAT1) sequences are shown in the following table:

| Transcript | Protein | Isoform encoded | Variant |
|---|---|---|---|
| NM_022787.4 | NP_073624.2 | isoform 1 | variant (1) |
| NM_001297778.1 | NP_001284707.1 | isoform 1 | variant (2) |
| NM_001297779.2 | NP_001284708.1 | isoform 2 | variant (3) |

Variant (1) encodes the longer isoform (1). Variant (2) differs in the 5' UTR, compared to variant 1. Variants 1 and 2 encode the same isoform (1). Variant (3) lacks an exon and contains an alternate 3' terminal exon, resulting in a different 3' coding region and 3' UTR, compared to variant 1. The encoded isoform (2) has a distinct C-terminus and is shorter than isoform 1.

In some embodiments, the sequence encoding NMNAT1 comprises SEQ ID NO: 2, or a sequence that is at least 80, 85, 90, 95, 97, 98, or 99% identical to SEQ ID NO: 2.

Human NMNAT1 Encoding Sequence

```
                                        (SEQ ID NO: 2)
atggaaaattccgagaagactgaagtggttctccttgcttgtggttcat tcaatcccatcaccaacatgcacctcaggttgtttgagctggccaagga ctacatgaatggaacaggaaggtacacagttgtcaaaggcatcatctct cctgttggtgatgcctacaagaagaaaggactcattcctgcctatcacc gggtcatcatggcagaacttgctaccaagaattctaaatgggtggaagt tgatacatgggaaagtcttcagaaggagtggaaagagactctgaaggtg ctaagacaccatcaagagaaattggaggctagtgactgtgatcaccagc agaactcacctactctagaaaggcctggaaggaagaggaagtggactga aacacaagattctagtcaaaagaaatccctagagccaaaaacaaaagct gtgccaaaggtcaagctgctgtgtggggcagatttattggagtcctttg ctgttcccaatttgtggaagagtgaagacatcacccaaatcgtggccaa ctatgggctcatatgtgttactcgggctggaaatgatgctcagaagttt atctatgaatcggatgtgctgtggaaacaccggagcaacattcacgtgg tgaatgaatggatcgctaatgacatctcatccacaaaaatccggagagc cctcagaagggccagagcattcgctacttggtaccagatcttgtccaa gaatacattgaaaagcataatttgtacagctctgagagtgaagacagga atgctggggtcatcctggcccctttgcagagaaacactgcagaagctaa gacatag
```

In some embodiments, the sequence encoding NMNAT1 can be codon optimized so that it can be more efficiently translated into an amino acid sequence. Codon usage tables for different organisms are known in the art. An exemplary codon-optimized NMNAT1-encoding sequence is presented in FIG. 1A/SEQ ID NO:1.

Sequences useful in the present methods, vectors, and compositions include those that encode a human NMNAT1 protein, or a protein that is at least 80, 85, 90, 95, 97, 98, or 99% identical to a human NMNAT1 protein. An exemplary human NMNAT1 protein sequence is presented in NP_073624.2, shown herein as SEQ ID NO:3.

Exemplary Human NMAT1 Protein Sequence (SEQ ID NO: 3)
MENSEKTEVVLLACGSFNPITNMHLRLFELAKDYMNGTGRYTVVKGIIS

PVGDAYKKKGLIPAYHRVIMAELATKNSKWVEVDTWESLQKEWKETLKV

LRHHQEKLEASDCDHQQNSPTLERPGRKRKWTETQDSSQKKSLEPKTKA

VPKVKLLCGADLLESFAVPNLWKSEDITQIVANYGLICVTRAGNDAQKF

IYESDVLWKHRSNIHVVNEWIANDISSTKIRRALRRGQSIRYLVPDLVQ

EYIEKHNLYSSESEDRNAGVILAPLQRNTAEAKT

In some embodiments, human NMNAT1 protein isoform 2 can be used, e.g., as provided at GenBank Ref. No. NP 001284708.1.

The human NMNAT1 protein can include one or more mutations, e.g., mutations at up to 1, 2, 3, 4, 5, 10, 15, or 20% of the residues. Such variants should retain the activity of the wild type protein, e.g., the ability to participate in regenerating NAD+ in cell nuclei. In some embodiments, the mutation is a conservative substitution. Such changes include substituting any of isoleucine (I), valine (V), and leucine (L) for any other of these hydrophobic amino acids; aspartic acid (D) for glutamic acid (E) and vice versa; glutamine (Q) for asparagine (N) and vice versa; and serine (S) for threonine (T) and vice versa. Other substitutions can also be considered conservative, depending on the environment of the particular amino acid and its role in the three-dimensional structure of the protein. For example, glycine (G) and alanine (A) can frequently be interchangeable, as can alanine (A) and valine (V). Methionine (M), which is relatively hydrophobic, can frequently be interchanged with leucine and isoleucine, and sometimes with valine. Lysine (K) and arginine (R) are frequently interchangeable in locations in which the significant feature of the amino acid residue is its charge and the differing pk's of these two amino acid residues are not significant. Still other changes can be considered "conservative" in particular environments (see, e.g. Table III of US 20110201052; pages 13-15 "Biochemistry" 2nd ED. Stryer ed (Stanford University); Henikoff et al., PNAS 1992 Vol 89 10915-10919; Lei et al., J Biol Chem 1995 May 19; 270 (20): 11882-6).

To determine the percent identity of two amino acid sequences, or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, the length of a reference sequence aligned for comparison purposes is at least 80% of the length of the reference sequence, and in some embodiments is at least 90% or 100%. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. For example, the percent identity between two amino acid sequences can determined using the Needleman and Wunsch ((1970) *J. Mol. Biol.* 48:444-453) algorithm which has been incorporated into the GAP program in the GCG software package (available on the world wide web at gcg.com), using the default parameters, e.g., a Blossum 62 scoring matrix with a gap penalty of 12, a gap extend penalty of 4, and a frameshift gap penalty of 5.

Methods

In clinical settings, the vectors can be introduced into a subject by any of a number of methods, each of which is familiar in the art. Although other methods can be used, in some embodiments, the route of choice for delivery of gene therapy vectors to the retina is via sub-retinal injection. This provides access to the RPE and photoreceptor cells of the retina. Different serotypes of AAV have been shown to transduce these cell populations effectively after sub-retinal injection in animal studies (Vandenberghe et al., PLOS One. 2013; 8:e53463. PMCID: 3559681; Vandenberghe and Auricchio, Gene Therapy. 2012; 19:162-8; Vandenberghe et al., Science translational medicine. 2011; 3: 88ra54; Dinculescu et al., HumGene Ther. 2005; 16:649-63; Boye et al., Mol Ther. 2013; 21:509-19; Alexander and Hauswirth, Adv Exp Med Biol. 2008; 613:121-8). The sub-retinal injection approach is being used in the ongoing clinical trials of gene augmentation therapy for retinal degeneration caused by mutations in the RPE65 and CHM genes genetic disease (Maguire et al., New England Journal of Medicine. 2008; 358:2240-8; Bainbridge et al., New England Journal of Medicine. 2008; 358:2231-9; Cideciyan et al., Proceedings National Academy Sciences USA. 2008; 105:15112-7; Maguire et al., Lancet. 2009; 374:1597-605; Jacobson et al., Archives Ophthalmology. 2012; 130:9-24; Bennett et al., Science translational medicine. 2012; 4: 120ra15; MacLaren et al., Lancet. 2014; 383:1129-37). Sub-retinal injections can be performed using a standard surgical approach (e.g., as described in Maguire et al., 2008 supra; Bainbridge et al., 2008 supra; Cideciyan et al., 2008 supra; MacLaren et al., 2014 supra).

Subjects

The present methods can be used to treat subjects who have NMNAT1-associated retinopathy/retinal degeneration, e.g., Leber congenital amaurosis or early-onset severe retinal dystrophy (EOSRD). Such subjects can be identified by one of skill in the art and a diagnosis confirmed by genetic testing (e.g., sequencing to identify the presence of a mutation in the subject's NMNAT1 gene). See, e.g., Kumaran et al., "Leber Congenital Amaurosis/Early-Onset Severe Retinal Dystrophy Overview" in Gene Reviews, Adam M P, Ardinger H H, Pagon R A, et al., editors. Seattle (WA): University of Washington, Seattle; 1993-2020; Kumaran et al., Retin Cases Brief Rep. 2018 Jul. 11. doi: 10.1097/ICB.0000000000000754.

EXAMPLES

The invention is further described in the following examples, which do not limit the scope of the invention described in the claims.

Materials and Methods

The following materials and methods were used in the Examples below.

Mouse Lines

The p. V9M-Nmnat1 mouse line was derived previously from an N-ethyl-N-nitrosourea (ENU) mutagenesis screen.[25] For the purpose of increasing fecundity, the original C57B1/6J line was alternately outcrossed with wildtype 129S6/SvEvTac mice (Taconic, Rensselaer, NY) and wildtype C57BL/6J mice (The Jackson Laboratory, Bar Harbor, ME) to maintain a mixed C57B1/6J-129S6 genetic background. Wildtype CD1-IGS mice (Charles River, Wilmington, MA), used only to screen for reagent component toxicity, were maintained separately. Male and female mice were used in experiments without preference.

Animal Husbandry

Mice were bred and maintained in the Schepens Eye Research Institute Animal Care Facility where they were fed 4% fat rodent diet and water ad libitum and housed in a 12-hour light/12-hour dark cycle. This study conformed to the Association for Research in Vision and Ophthalmology Statement for the Use of Animals in Ophthalmic and Vision Research, and all procedures were approved by the Animal Care and Use Committee of the Schepens Eye Research Institute.

Genotyping

A tissue biopsy was prepared for polymerase chain reaction (PCR) using Allele-In-One Mouse Tail Direct Lysis Buffer (Allele Biotech, San Diego, CA) according to the manufacturer's instructions. PCR was carried out using the forward primer 5'-CATGGCTGTGCTGAGGTG-'3 (intron 1; SEQ ID NO:4) and reverse primer 5'-AACAGCCT-GAGGTGCATGTT-'3 (exon 2; SEQ ID NO:5) to amplify a 691 bp region of Nmnat1 that includes codon 9. The 20 µL PCR reactions had final concentrations of 200 µmol/L for each primer, 200 nmol/L for each of the dNTPs (dATP, dGTP, dTTP, and dCTP), 2 mmol/L MgCl2, and 1 unit of Hot FirePol DNA polymerase (Solis BioDyne, Tartu, Estonia). The thermocycling protocol was 95° C. for 14 minutes; 30 cycles of 95° C. for 45 seconds, 53° C. for 45 seconds, 72° C. for 30 seconds; 72° C. for 7 minutes. Next, the amplified product was subjected to Sanger sequencing using primer 5'-ACGTATTTGCCCACCTGTCT-'3; SEQ ID NO:6, and the electropherograms were analyzed at c.25 to identify each mouse as being wildtype, heterozygous, or homozygous for Nmnat1$^{V9M}$.

DNA Construct and AAV Vector Preparation

A codon-optimized human NMNAT1 cDNA (FIG. 1A), designed by DNA 2.0 (Menlo Park, CA) and synthesized into a gBlock gene fragment (Integrated DNA Technologies, Coralville, IA), was incorporated into constructs that were then packaged into recombinant AAV viral vectors.

Plasmids containing the full constructs were generated using standard endotoxin-free molecular cloning techniques and validated by sequencing NMNAT1 and regions crossing ligation sites.

AAV was prepared by the Grousbeck Gene Therapy Center of Massachusetts Eye and Ear, as described previously.[34] Purified virus was collected in a final buffer containing 1×PBS, 35 mM NaCl, and 0.001% Pluronic F68 surfactant and then titered. The same buffer was used to further dilute the virus, if required, to achieve the target dose. To assist with the injection procedure, <0.25% of fluorescein (AK-Fluor, Akorn, Lake Forest, IL) was mixed into the working solution as a tracer.

To troubleshoot AAV2/Anc80 reagent toxicity, injections were performed using specific modifications: 1) AAV2/Anc80 was manufactured with surfactant added only after production, 2) AAV2/Anc80 was diluted in low salt dilution buffer, 3) Saline only (vector removed), 4) Saline plus a 100× concentration of the surfactant (vector removed), 5) Saline (vector removed) with fluorescein.

General Anesthesia

For general anesthesia, a mixture of ketamine/xlyazine was delivered by intraperitoneal injection. Two-week-old mice received a dose of 37.5 mg/kg ketamine and 3.8 mg/kg xylazine and adult mice received a dose of 100 mg/kg ketamine and 20 mg/kg xylazine. To counteract the formation of permanent anesthesia-induced corneal opacities, a 2 mg/kg dose of Yohimbine HCL (Wedgewood Pharmacy, Swedesboro, NJ) was administered by subcutaneous injection immediately following each recovery procedure in which ketamine/xylazine was used (i.e., AAV injection, in vivo imaging, ERG).[51,52] For neonatal mice, general anesthesia by hypothermia was induced by indirect exposure to ice.[53]

Virus Delivery

In two-week-old mice, the Micro4 microinjection pump with RPE kit (World Precision Instruments, Sarasota, FL) was used to deliver the viral reagents into either the subretinal space or the vitreous chamber. Pupils were dilated using either Tropicamide (1%) or a half mixture of Tropicamide (0.25%), Phenyephrine hydrochloride (0.25%), and Cyclepentalate (1%). Mice were deeply anesthetized with ketamine/xylazine and local anesthesia was administered topically using Proparacaine hydrochloride (0.5%). Next, the eye was proposed and a 30 g syringe needle was used to puncture the superior-temporal sclera and retina immediately posterior to the episcleral vessels of limbus to make an entry route for a blunt-end 33 g cannula.

For subretinal injections, the traversal of the cannula through the vitreous chamber was visualized via a dissecting microscope through the dilated pupil and the cannula tip was positioned in the subretinal space of the posterior part of the inferior-nasal quadrant of the eye. Four successive 185.5 nL boluses of reagent (0.75 µL total) were injected, and the formation of a bleb was confirmed by visualization that was enhanced by the fluorescein tracer. The cannula was held in place for approximately three seconds following injection to avoid reflux of the reagent and then gently removed from the eye. Finally, the entry wound was treated by tamponade with a cotton swab. The eyes were then hydrated with artificial tears (Blink Tears, Abbott Laboratories, Chicago, IL), and the mice recovered from anesthesia on a heating pad.

The procedure for intravitreal injection of two-week-old mice was identical, except that the cannula tip was positioned in the center of the vitreous chamber during injection.

In neonates, subretinal injections were performed using the FemtoJet 4i microinjection system (Eppendorf, Hamburg, Germany). While the mice were anesthetized on ice, the tip of a 30 g hypodermic needle was used to separate the upper and lower eyelids. The eye was proposed and a custom beveled glass needle (Cat #C060609, Origio, Trumbull, CT) was directly inserted through the sclera and positioned in the underlying subretinal space. A single bolus of 0.5 µL of reagent was administered at pressure of 330 hPa over 6 seconds, after which the needle was held in place for approximately three seconds to avoid reflux and then gently removed. The mice recovered from anesthesia on a heating pad.

In Vivo Retinal Imaging

En face and cross-sectional images of the retina were acquired using fundus photography and spectral domain optical coherence tomography (OCT) (FIG. 2), as described previously.[25] An addition to the fundus photography procedure was that some images were taken through a filter that allows visualization of EGFP and therefore early evaluation of injection quality. Also, the rectangular volume scans were taken at multiple locations across the retina so that inferior and superior regions could be measured accurately, and ten scans were registered/averaged to generate the final images. Using in In VivoVue OCT software (Bioptogen), four approximately equally spaced caliper measurements were made from the outer plexiform layer to the retinal pigment epithelium to measure photoreceptor layer thickness.

Electroretinography

Full-field, flash electroretinograms were collected from the mice as described previously.[25] Briefly, mice were dark adapted overnight, and rod and mixed rod/cone responses were generated using a 0.01 cd·s/m$^2$ (scotopic) and 10 cd·s/m$^2$ (scotopic) broadband light stimuli, respectively. Next, the mice were light adapted by exposure to a steady 30 cd/m$^2$ (photopic) broadband light for 10 minutes, and this light remained on in the background during the acquisition of cone-isolated responses to a 20 cd·s/m$^2$ (photopic) broadband light stimulus.

Statistics

Statistical analyses were completed in Prism version 8.2.1 (GraphPad, San Diego, CA). For OCT and electroretinogram (ERG) time courses, a two-way ANOVA using a mixed effects regression model was performed. When analyzing the effect of treatment, the inferior retina of the non-injected eye was used as the negative control to which the means all other measurements were compared. The Dunnett post hoc test was used to account for Type I error generated from multiple comparisons testing. When analyzing the effects of injection and all quantitative data are reported as the mean±S.E.M.

Custom Anti-Human NMNAT1 Antibody Development

Purified, full-length human NMNAT1 was used by Aves Labs (Tigard, OR) as the antigen to generate a custom polyclonal antibody in chicken. This antibody reacts strongly against human NMNAT1 with minimal cross-reactivity with the mouse ortholog. In FIG. 6, the nuclei of human-derived ARPE-19 cells[54] counterstained with DAPI, showed robust antibody labeling consistent with NMNAT1 localization (top row). In mouse retina, the immunofluorescence was minimal (middle row), unless treated with AAV such that it expressed human NMNAT1 (bottom row); in the latter case, immunoreactivity was strong and localized to cell nuclei.

Ex Vivo Retinal Imaging
Immunohistochemistry

Mice were euthanized by $CO_2$ asphyxiation and immediately perfused through the heart using a Masterflex peristaltic pump (Cole-Parmer, Vernon Hills, IL). Each animal was perfused first with 0.13 mol/L phosphate-buffered saline (PBS) pH 7.2 to 7.4 that contained 2 U heparin/mL until the perfusate became clear, and this was followed by perfusion of ~40 mL of 2% paraformaldehyde (PFA). Both solutions were warmed to ~37° C. at the time of perfusion. A small vessel cauterizer (#18000-00, Fine Science Tools, Foster City, CA) was used to mark the cornea immediately anterior to the superior limbus. Eyes were enucleated, incubated at 2% PFA for 0.5 hr at room temperature, the anterior segment was removed, and then the remaining eye cup was incubated once again in 2% PFA for 0.5 hr at room temperature before being immersed in 30% sucrose at room temperature for at least one hour. Eye cups were embedded, sectioned at 10 μL thickness by cryotomy, immunolabeled and stained, and imaged in either fluorescence or bright-field mode using the Eclipse Ti fluorescence microscope (Nikon, Tokyo, Japan) as described previously,[25] unless otherwise imaged with the TCS SP8 confocal microscope (Leica, Wetzlar, Germany).

Hemotoxylin & Eosin Labeling

Eyes were enucleated following euthanasia by $CO_2$ asphyxiation, washed in PBS, immediately submerged in O-fix tissue fixative [<70% ethanol, <5% methanol, <7% acetic acid, <4% acetic acid, and 4% formaldehyde] (Leica, 3800676), and incubated in the fixative overnight. Samples were then dehydrated in a series of graded ethyl alcohols, cleared in xylenes, and embedded in paraffin (Paraplast Plus, McCormick Scientific, Richmond, IL). 6 μm thick sections were prepared using a Leica RM2145 microtome (Leica Biosystems, Buffalo Grove, IL) and then slides were stained with Gill's #2 Hematoxylin and Eosin-y (Fisher Scientific, Pittsburgh, PA USA) prior to being coverslipped with Permount mounting media.

Example 1. DNA Construct and AAV Reagent Preparation

A codon-optimized human NMNAT1 cDNA (FIG. 1A) was incorporated into constructs that were then packaged into recombinant AAV viral vectors. Codon optimization has been found to improve the level and duration of expression for human genes in transduced cells without altering the amino acid sequence of the protein product[26-30]. Likewise, all 174 nucleotide substitutions introduced into the 840 bp NMNAT1 cDNA were silent, defining the normal human protein sequence.

Four DNA constructs and six AAV vectors subtypes were used in combination to create four reagents that were delivered to mice as part of this study. A construct in which NMNAT1 was driven by the ubiquitously expressing CASI promoter was packaged into both a self-complementary (SC) and single-stranded (SS) version of AAV2/9. The SC vector was selected for testing because it activates gene expression more rapidly than traditional SS vectors.[31] Moreover, a construct containing an EGFP (enhanced green fluorescent protein) reporter gene, driven also by the CASI promoter and followed by WPRE (woodchuck hepatitis virus posttranslational regulatory element) that serves to enhance AAV2 mediated transduction in mouse retina,[32] was packaged into SS.AAV2/9. This EGFP reagent was spiked in with the SC.AAV2/9 reagent (FIG. 1B) and SS.AAV2/9 reagent (FIG. 1C) at 1×10$^8$ genomic copies per microliter (gc/μL) just before delivery to the mice so that gene expression could be confirmed by in vivo and ex vivo imaging. Another construct was made which NMNAT1 was driven by the ubiquitously expressing CAG promoter and followed by a T2A cleavage sequence, EGFP, and then WPRE. After translation in the cell, the NMNAT1-EGFP fusion protein was enzymatically separated at the T2A cleavage site[33] to avoid disruption of nominal protein conformations and kinetics. The construct was packaged into AAV2/Anc80, a synthetic AAV2 that was generated by directed evolution to circumvent innate immunity and has been shown to transduce retinal cells efficiently in mice (FIG. 1D).[34] Finally, the same CASI.NMNAT1 construct described above was packaged into the AAV2/7m[8] vector that, unlike the other vectors, can be delivered to all retinal layers by intravitreal injection (FIG. 1E).[35]

Example 2. Gene Augmentation Using the Self-Complementary Vector Preserves Retinal Structure Administering gene augmentation therapy to Nmnat1l94/19M mice at two weeks of age using the self-complementary (SC) AAV2/9 (SC.AAV2/9) reagent stably preserved retinal structure in Nmnat1$^{V9M/V9M}$ mice in a dose-dependent manner. This finding was determined by photoreceptor layer thickness measurements collected in vivo using optical coherence tomography (OCT). For injected eyes, measurements were taken proximal to the injection site in the inferior retina where rescue was anticipated to be most robust and in the superior retina that was distal from the injection site. Measurements in the non-injected fellow eyes of the Nmnat1$^{V9M/V9M}$ mice and in the non-injected eyes of age-matched littermate controls were acquired in the inferior retina in the plane equivalent to where the measurements were taken in the injected eyes (FIG. 2).

Middle and high titer injection, $1\times10^8$ (gc/μL) and $2\times10^9$ gc/μL, respectively, both provided significant rescue across the injected retina (FIG. 3A, top row). For example, at nine months of age, eyes injected with the $2\times10^9$ gc/μL dose had inferior and superior photoreceptor layer thicknesses of 100.0 μm±4.8 (68.7 μm difference, p<0.0001) and 96.1 μm±6.4 (64.8 μm difference, p<0.0001), respectively, compared to the 31.3 μm±0.8 thick inferior region of the fellow non-injected eyes. The treated retinas were typically within ~20% of the thickness of the inferior wildtype retina. Photoreceptor layer thickness tended to be similar (p>0.05) between the inferior retina (proximal to the injection site) and the superior retina (distal to the injection site) following the $2\times10^9$ gc/μL dose. However, retinal thickness decreased by ~20% with distance from the injection site following the $1\times10^8$ gc/μL dose. We could not test whether doses greater than $2\times10^9$ gc/μL would provide an additional advantage since this was the full-strength preparation.

At $1\times10^7$ (gc/μL), the lowest dosage tested for this reagent, a modest rescue of photoreceptor layer thickness was observed in the inferior region (proximal to the injection site) of the Nmnat1$^{V9M/V9M}$ retina, as compared to the fellow non-injected retina. This finding reached statistical significance at four and six months only, showing differences of 25.8 μm±6.5 (p=0.014) and 30.2 μm±7.9 (p=0.035) from the inferior region of the fellow retina, respectively. The photoreceptor layer of the rescued region only had approximately half the thickness of the equivalent region of the non-injected wildtype littermate control retina, and at no timepoint did the retinal region distal to the injection site (i.e., superior retina) show evidence of rescue.

Because the loss of NMNAT1 activity may differ greatly by mutation, understanding whether overexpression of NMNAT1 is important. For this purpose, wildtype mice were injected with the SC.AAV2/9 reagent at the same titers as the mutant littermates. Across all dosages and time points, photoreceptor layer thickness was typically unaffected, with differences that were statistically significant being noted in only three instances (FIG. 3A, bottom row).

The largest disparity was in the superior region of the injected retina at nine months following a $2\times10^9$ gc/μL injection in which a decrease of 17.9 μm±6.9 (p=0.039) was measured. However, given that the inferior region (proximal to the injection site) of the same retina was unaffected, the decrement was unlikely due to toxicity.

Example 3. Single-Stranded Vectors do not Rescue Disease Phenotype

In contrast to the SC.AAV2/9 reagent, the SS.AAV2/9, AAV2/7m[8], and AAV2/Anc80 reagents did not provide stable structural rescue of the Nmnat1$^{V9M/V9M}$ retina. At two months of age, the inferior region of mutant retinas injected with the SS.AAV2.9 reagent showed a very modest rescue of 11.4 μm±4.3 (p=0.033) over the same region of the non-injected fellow eye (FIG. 3B), and the AAV2/7m[8] reagent had no effect. The $5.5\times10^8$ gc/μL dose of the AAV2/Anc80 reagent produced a transient rescue in the mutant retina that did not persist beyond two months of age and was confined to the inferior region. At the 1.5- and 2-month time points, respectively, the inferior region of AAV2/Anc80 treated retinas had photoreceptor thicknesses that were 42.0 μm±3.7 (p=0.0005) and 27.5 μm±9.9 (p=0.045) greater than that of the untreated fellow retinas (FIG. 3C). No rescue was observed when dosage was decreased to $1\times10^8$ gc/μL and increasing the AAV2/Anc80 reagent dosage to $\geq1\times10^9$ gc/μL failed due to toxicity. In both wildtype and NMNAT1$^{V9M/V9M}$ retina, high titer injections of the AAV2/Anc80 reagent caused retinal degeneration, appearance of intravitreal cellular infiltrates,[36,37] and severe retinal detachment by age six weeks (FIG. 4). To test whether components of the dilution buffer used with the AAV2/Anc80 reagent contributed to this outcome, components of this solution were injected into wildtype mice under different conditions. Modulating the surfactant, salt, and fluorescein concentrations did not cause retinal damage detectable by OCT or histology (data not shown).

The structural rescue of the NMNAT1$^{V9M/V9M}$ retina associated with the SC.AAV2 reagent, as observed by OCT, was confirmed ex vivo by light microscopy. Hematoxylin and eosin (H&E) staining confirmed that, in stark contrast to the untreated mutant retina, the well-transduced regions of rescued retinas had all cell types intact and had elaborated photoreceptor outer segments (FIG. 5A). The retinal layers of the treated mutant retina, however, appeared slightly thinner than the non-treated wildtype retina, which was consistent with the aforementioned measurements from OCT images. While the injected wildtype retinas were often indistinguishable from the non-injected fellow retina, regions existed where the photoreceptor outer segments were partially retracted and other retinal layers were thinner. Immunolabeling experiments showed that transgene expression was detectable in the nucleus of nearly every type of retinal cell in both injected mutant and wildtype retinas (FIG. 5B).

Furthermore, the pan-retinal transgene expression often extended beyond two-thirds of the tissue (FIG. 3B). Immunolabeling was completed using a custom chicken polyclonal α-human NMNAT1 antibody that has minimal cross-reactivity with mouse NMNAT1 (FIG. 6).

Example 4. Gene Augmentation Using a Self-Complementary Vector Preserves Retinal Function To assess whether the structural rescue of the retina translated to preservation of function, rod, mixed rod/cone, and cone-isolated responses to light stimulation were measured in vivo by ERG, a non-invasive procedure used to measure the electrical response of the retina to light stimulation. Specifically, the magnitude of the ERG b-wave, which is mediated by ON bipolar cells,[38,39] was used as an indirect indicator of the photoreceptor response[40] as well as a measure of inner retinal function. For retinas treated with the SC.AAV2/9 reagent, the b-wave was significantly greater than that of the untreated fellow eye by age four months and remained so through age six months for photopic stimuli and at least nine months for scotopic and mixed rod/cone stimuli. The photopic ERGs tended to be greater in the treated mutant retina at age nine months than in the untreated fellow retina (FIG. 7A, Top row). For example, at six months, the response of the treated mutant retina exceeded that of the fellow retina for each condition: 156.1 µV±23.4 versus 36.0 µV±7.1 (p=0.0013) for the rod response, 293.6 µV±51.1 versus 62.0±11.8 (p=0.0034) for the mixed rod/cone response, and 101.3 µV±18.6 versus 25.3±6.2 (p=0.0067) for the cone response.

Moreover, the responses associated with rescue were consistently lower than those of the untreated wildtype retinas. This effect may have originated from two sources. First, the OCT and histological images showed that even the most robust structural rescue was incomplete.

Second, the injection itself appeared to dampen ERG signals since the injected wildtype retinas generated ERGs with amplitudes that tended to be smaller than those of the fellow retinas.

Regardless, for each stimulation condition, the structure and implicit times of the rescued ERG waveforms were normal (FIG. 7A, Bottom row). The SC.AAV2 reagent at $1 \times 10^8$ gc/µL showed evidence of rescue in the injected mutant retina (FIG. 7B, Top row), whereas no sign of rescue by the AAV2/Anc80 reagent was observed at age two months when there was preservation of structure FIG. 7B, Bottom row).

Example 5. Self-Complementary Vector Activates NMNAT1 Expression Earlier than Single-Stranded Vectors To understand why retinal structural and function was preserved to a greater extent when the transgene was delivered via the SC.AAV2/9 vector, we characterized early NMNAT1 expression profiles. At fourteen days post-injection, immunolabeling of NMNAT1 delivered by SC.AAV2/9 was detectable in all retinal layers with particularly high density in the outer nuclear layer (ONL) (FIG. 8A). Conversely, in SS.AAV2/9 and AAV2/Anc80 injected retinas, detection of NMNAT1 was sparse with relatively few photoreceptors labeled, even though the SS.AAV2/9 vector carries identical cargo and the AAV2/Anc80 vector has been shown to transduce the mouse retina photoreceptors with wide coverage.[34] NMNAT1 was undetectable at seven days post-injection, regardless of the delivery vector used.

Example 9. A Successful Intervention Requires Transduction of Photoreceptors

Furthermore, to determine whether an earlier intervention would produce better efficacy from the AAV2/Anc80 reagent, injections were performed in neonatal mice at postnatal day 0 (P0) through P2. While most cell types showed strong NMNAT1 expression, including cone photoreceptors, expression in rod photoreceptors was overwhelmingly weak (FIG. 8B); cone photoreceptors were distinguished by the location of their nuclei in the outermost rows of the ONL.[41] Similarly, preservation of the photoreceptor layer was not observed four weeks after intravitreal delivery of NMNAT1 via AAV2/7m[8] in two-week-old mice by OCT, and it was determined by immunohistochemistry that NMNAT1 expression was absent in the outer retina, despite a strong inner retina signal (FIG. 8C).

REFERENCES

1. Chiang, P W, Wang, J, Chen, Y, Fu, Q, Zhong, J, Chen, Y, et al. (2012). Exome sequencing identifies NMNAT1 mutations as a cause of Leber congenital amaurosis. Nat Genet 44:972-974.
2. Koenekoop, R K, Wang, H, Majewski, J, Wang, X, Lopez, I, Ren, H, et al. (2012). Mutations in NMNAT1 cause Leber congenital amaurosis and identify a new disease pathway for retinal degeneration. Nat Genet 44:1035-1039.
3. Perrault, I, Hanein, S, Zanlonghi, X, Serre, V, Nicouleau, M, Defoort-Delhemmes, S, et al. (2012). Mutations in NMNAT1 cause Leber congenital amaurosis with early-onset severe macular and optic atrophy. Nat Genet 44:975-977.
4. Falk, M J, Zhang, Q, Nakamaru-Ogiso, E, Kannabiran, C, Fonseca-Kelly, Z, Chakarova, C, et al. (2012). NMNAT1 mutations cause Leber congenital amaurosis. Nat Genet 44:1040-1045.
5. Nash, B M, Symes, R, Goel, H, Dinger, M E, Bennetts, B, Grigg, J R, et al. (2018). NMNAT1 variants cause cone and cone-rod dystrophy. Eur J Hum Genet 26:428-433.
6. Garavaglia, S, D'Angelo, I, Emanuelli, M, Carnevali, F, Pierella, F, Magni, G, et al. (2002). Structure of human NMN adenylyltransferase. A key nuclear enzyme for NAD homeostasis. J Biol Chem 277:8524-8530.
7. Belenky, P, Bogan, K L, and Brenner, C (2007). NAD+ metabolism in health and disease. Trends Biochem Sci 32:12-19.
8. Lau, C, Niere, M, and Ziegler, M (2009). The NMN/NaMN adenylyltransferase (NMNAT) protein family. Front Biosci (Landmark Ed) 14:410-431.
9. Chiarugi, A, Dolle, C, Felici, R, and Ziegler, M (2012). The NAD metabolome—a key determinant of cancer cell biology. Nat Rev Cancer 12:741-752.
10. Sasaki, Y, Margolin, Z, Borgo, B, Havranek, J J, and Milbrandt, J (2015). Characterization of Leber's Congenital Amaurosis-associated NMNAT1 Mutants. J Biol Chem.
11. Coppieters, F, Todeschini, A L, Fujimaki, T, Baert, A, De Bruyne, M, Van Cauwenbergh, C, et al. (2015). Hidden Genetic Variation in LCA9-Associated Congenital Blindness Explained by 5'UTR Mutations and Copy-Number Variations of NMNAT1. Hum Mutat 36:1188-1196.
12. Conforti, L, Janeckova, L, Wagner, D, Mazzola, F, Cialabrini, L, Di Stefano, M, et al. (2011). Reducing expression of NAD+ synthesizing enzyme NMNAT1 does not affect the rate of Wallerian degeneration. FEBS J 278:2666-2679.
13. Berger, F, Lau, C, Dahlmann, M, and Ziegler, M (2005). Subcellular compartmentation and differential catalytic properties of the three human nicotinamide mononucleotide adenylyltransferase isoforms. J Biol Chem 280:36334-36341.
14. Carvalho, L S, and Vandenberghe, L H (2015). Promising and delivering gene therapies for vision loss. Vision Res 111:124-133.
15. Ong, T, Pennesi, M E, Birch, D G, Lam, B L, and Tsang, S H (2019).

Adeno-Associated Viral Gene Therapy for Inherited Retinal Disease. Pharm Res 36:34.
16. McCarty, D M (2008). Self-complementary AAV vectors; advances and applications. Mol Ther 16:1648-1656.
17. Lloyd, A, Piglowska, N, Ciulla, T, Pitluck, S, Johnson, S, Buessing, M, et al. (2019). Estimation of impact of RPE65-mediated inherited retinal disease on quality of life and the potential benefits of gene therapy. Br J Ophthalmol 103:1610-1614.
18. Lam, B L, Davis, J L, Gregori, N Z, MacLaren, R E, Girach, A, Verriotto, J D, et al. (2019). Choroideremia Gene Therapy Phase 2 Clinical Trial: 24-Month Results. Am J Ophthalmol 197:65-73.
19. Ghazi, N G, Abboud, E B, Nowilaty, S R, Alkuraya, H, Alhommadi, A, Cai, H, et al. (2016). Treatment of retinitis pigmentosa due to MERTK mutations by ocular subretinal injection of adeno-associated virus gene vector: results of a phase I trial. Hum Genet 135:327-343.
20. Cukras, C, Wiley, H E, Jeffrey, B G, Sen, H N, Turriff, A, Zeng, Y, et al. (2018). Retinal AAV8-RS1 Gene Therapy for X-Linked Retinoschisis: Initial Findings from a Phase I/IIa Trial by Intravitreal Delivery. Mol Ther 26:2282-2294.
21. Dyka, F M, Molday, L L, Chiodo, V A, Molday, R S, and Hauswirth, W W (2019). Dual ABCA4-AAV Vector Treatment Reduces Pathogenic Retinal A2E Accumulation in a Mouse Model of Autosomal Recessive Stargardt Disease. Hum Gene Ther 30:1361-1370.
22. Mccullough, K T, Boye, S L, Fajardo, D, Calabro, K, Peterson, J J, Strang, C E, et al. (2019). Somatic Gene Editing of GUCY2D by AAV-CRISPR/Cas9 Alters Retinal Structure and Function in Mouse and Macaque. Hum Gene Ther 30:571-589.
23. Alves, C H, and Wijnholds, J (2018). AAV Gene Augmentation Therapy for CRB1-Associated Retinitis Pigmentosa. Methods Mol Biol 1715:135-151.
24. Ofri, R, Averbukh, E, Ezra-Elia, R, Ross, M, Honig, H, Obolensky, A, et al. (2018). Six Years and Counting: Restoration of Photopic Retinal Function and Visual Behavior Following Gene Augmentation Therapy in a Sheep Model of CNGA3 Achromatopsia. Hum Gene Ther.
25. Greenwald, S H, Charette, J R, Staniszewska, M, Shi, L Y, Brown, S D, Stone, L, et al. (2016). Mouse Models of NMNAT1-Leber Congenital Amaurosis (LCA9) Recapitulate Key Features of the Human Disease. Am J Pathol 186:1925-1938.
26. Burgess-Brown, N A, Sharma, S, Sobott, F, Loenarz, C, Oppermann, U, and Gileadi, O (2008). Codon optimization can improve expression of human genes in *Escherichia coli*: A multi-gene study. Protein Expr Purif 59:94-102.
27. Gustafsson, C, Govindarajan, S, and Minshull, J (2004). Codon bias and heterologous protein expression. Trends Biotechnol 22:346-353.
28. Ill, C R, and Chiou, H C (2005). Gene therapy progress and prospects: recent progress in transgene and RNAi expression cassettes. Gene Ther 12:795-802.
29. Foster, H, Sharp, P S, Athanasopoulos, T, Trollet, C, Graham, I R, Foster, K, et al. (2008). Codon and mRNA sequence optimization of microdystrophin transgenes improves expression and physiological outcome in dystrophic mdx mice following AAV2/8 gene transfer. Mol Ther 16:1825-1832.
30. Sack, B K, Merchant, S, Markusic, D M, Nathwani, A C, Davidoff, A M, Byrne, B J, et al. (2012). Transient B cell depletion or improved transgene expression by codon optimization promote tolerance to factor VIII in gene therapy. PLOS One 7: e37671.
31. McCarty, D M, Monahan, P E, and Samulski, R J (2001). Self-complementary recombinant adeno-associated virus (scAAV) vectors promote efficient transduction independently of DNA synthesis. Gene Ther 8:1248-1254.
32. Patricio, M I, Barnard, A R, Orlans, H O, McClements, M E, and MacLaren, R E (2017). Inclusion of the Woodchuck Hepatitis Virus Posttranscriptional Regulatory Element Enhances AAV2-Driven Transduction of Mouse and Human Retina. Mol Ther Nucleic Acids 6:198-208.
33. Kim, J H, Lee, S R, Li, L H, Park, H J, Park, J H, Lee, K Y, et al. (2011). High cleavage efficiency of a 2A peptide derived from porcine teschovirus-1 in human cell lines, zebrafish and mice. PLOS One 6: e18556.
34. Zinn, E, Pacouret, S, Khaychuk, V, Turunen, H T, Carvalho, L S, Andres-Mateos, E, et al. (2015). In Silico Reconstruction of the Viral Evolutionary Lineage Yields a Potent Gene Therapy Vector. Cell Rep 12:1056-1068.
35. Dalkara, D, Byrne, L C, Klimczak, R R, Visel, M, Yin, L, Merigan, W H, et al. (2013). In vivo-directed evolution of a new adeno-associated virus for therapeutic outer retinal gene delivery from the vitreous. Sci Transl Med 5: 189ra176.
36. Zarranz-Ventura, J, Keane, P A, Sim, D A, Llorens, V, Tufail, A, Sadda, S R, et al. (2016). Evaluation of Objective Vitritis Grading Method Using Optical Coherence Tomography: Influence of Phakic Status and Previous Vitrectomy. Am J Ophthalmol 161:172-180 e171-174.
37. Saito, M, Barbazetto, I A, and Spaide, R F (2013). Intravitreal cellular infiltrate imaged as punctate spots by spectral-domain optical coherence tomography in eyes with posterior segment inflammatory disease. Retina 33:559-565.
38. Stockton, R A, and Slaughter, M M (1989). B-wave of the electroretinogram. A reflection of O N bipolar cell activity. J Gen Physiol 93:101-122.
39. Bush, R A, and Sieving, P A (1996). Inner retinal contributions to the primate photopic fast flicker electroretinogram. J Opt Soc Am A Opt Image Sci Vis 13:557-565.
40. Greenwald, S H, Kuchenbecker, J A, Roberson, D K, Neitz, M, and Neitz, J (2014). S-opsin knockout mice with the endogenous M-opsin gene replaced by an L-opsin variant. Vis Neurosci 31:25-37.
41. Carter-Dawson, L D, and La Vail, M M (1979). Rods and cones in the mouse retina. I I. Autoradiographic analysis of cell generation using tritiated thymidine. J Comp Neurol 188:263-272.
42. Carter, B J, Khoury, G, and Rose, J A (1972). Adenovirus-associated virus multiplication. I X. Extent of transcription of the viral genome in vivo. J Virol 10:1118-1125.
43. Sipo, I, Fechner, H, Pinkert, S, Suckau, L, Wang, X, Weger, S, et al. (2007). Differential internalization and nuclear uncoating of self-complementary adeno-associated virus pseudotype vectors as determinants of cardiac cell transduction. Gene Ther 14:1319-1329.
44. Wang, J, Xie, J, Lu, H, Chen, L, Hauck, B, Samulski, R J, et al. (2007). Existence of transient functional double-stranded DNA intermediates during recombinant AAV transduction. Proc Natl Acad Sci USA 104:13104-13109.
45. Petit, L, Ma, S, Cheng, S Y, Gao, G, and Punzo, C (2017). Rod Outer Segment Development Influences AAV-Mediated Photoreceptor Transduction After Subretinal Injection. Hum Gene Ther 28:464-481.

46. Xiong, W, MacColl Garfinkel, A E, Li, Y, Benowitz, L I, and Cepko, C L (2015). NRF2 promotes neuronal survival in neurodegeneration and acute nerve damage. J Clin Invest 125:1433-1445.
47. Geller, A M, Sieving, P A, and Green, D G (1992). Effect on grating identification of sampling with degenerate arrays. J Opt Soc Am A 9:472-477.
48. Geller, A M, and Sieving, P A (1993). Assessment of foveal cone photoreceptors in Stargardt's macular dystrophy using a small dot detection task. Vision Res 33:1509-1524.
49. Xiong, W, Wu, D M, Xue, Y, Wang, S K, Chung, M J, Ji, X, et al. (2019). AAV cis-regulatory sequences are correlated with ocular toxicity. Proc Natl Acad Sci USA 116:5785-5794.
50. Pawlyk, B S, Bulgakov, O V, Liu, X, Xu, X, Adamian, M, Sun, X, et al. (2010). Replacement gene therapy with a human RPGRIP1 sequence slows photoreceptor degeneration in a murine model of Leber congenital amaurosis. Hum Gene Ther 21:993-1004.
51. Turner, P V, and Albassam, M A (2005). Susceptibility of rats to corneal lesions after injectable anesthesia. Comp Med 55:175-182.
52. Koehn, D, Meyer, K J, Syed, N A, and Anderson, M G (2015). Ketamine/Xylazine-Induced Corneal Damage in Mice. PLOS One 10: e0132804.
53. Phifer, C B, and Terry, L M (1986). Use of hypothermia for general anesthesia in preweanling rodents. Physiol Behav 38:887-890.
54. Dunn, K C, Aotaki-Keen, A E, Putkey, F R, and Hjelmeland, L M (1996). ARPE-19, a human retinal pigment epithelial cell line with differentiated properties. Exp Eye Res 62:155-169.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of treating retinal degeneration caused by mutations in a nicotinamide mononucleotide adenylyltransferase 1 (NMNAT1) gene in a human subject, the method comprising delivering to an eye of the subject a therapeutically effective amount of an Adeno-associated virus 2/9 (AAV2/9) vector comprising a sequence encoding a functional human NMNAT1, operably linked to a CASI promoter that drives expression in photoreceptors, wherein the sequence encoding the functional human NMNAT1 is at least 98% identical to SEQ ID NO: 1.

2. The method of claim 1, wherein the sequence encoding the functional human NMNAT1 is codon optimized.

3. The method of claim 1, wherein the vector is delivered via sub-retinal injection.

4. The method of claim 1, wherein the vector is self-complementary AAV2/9 (scAAV2/9).

5. The method of claim 1, wherein the sequence encoding the functional human NMNAT1 is at least 99% identical to SEQ ID NO: 1.

6. The method of claim 1, wherein the sequence encoding the functional human NMNAT1 comprises SEQ ID NO:1.

7. The method of claim 1, wherein the vector further comprises a 3' bovine growth hormone untranslated region.

8. A method of increasing expression of NMNAT1 in photoreceptor cells in an eye of a human subject, the method comprising delivering to the eye of the subject a therapeutically effective amount of an Adeno-associated virus type 2/9 (AAV2/9) vector comprising a sequence encoding a functional human NMNAT1, operably linked to a CASI promoter that drives expression in the photoreceptor cells, wherein the subject has retinal degeneration caused by a mutation in a nicotinamide mononucleotide adenylyltransferase 1 (NMNAT1) gene, wherein the sequence encoding the functional human NMNAT1 is at least 97% identical to SEQ ID NO: 1.

9. The method of claim 8, wherein the vector is delivered via sub-retinal injection.

10. The method of claim 8, wherein the vector is self-complementary AAV2/9 (scAAV2/9).

11. The method of claim 8, wherein the sequence encoding the functional human NMNAT1 is at least 98% identical to SEQ ID NO:1.

12. The method of claim 8, wherein the sequence encoding the functional human NMNAT1 is at least 99% identical to SEQ ID NO: 1.

13. The method of claim 8, wherein the sequence encoding the functional human NMNAT1 comprises SEQ ID NO:1.

14. An Adeno-associated virus type 2/9 (AAV2/9) vector comprising a sequence encoding a functional human NMNAT1, operably linked to a CASI promoter that drives expression in photoreceptor cells, wherein the sequence encoding the functional human NMNAT1 is codon at least 98% identical to SEQ ID NO: 1.

15. The AAV2/9 vector of claim 14, wherein the vector is a self-complementary AAV2/9 (scAAV2/9).

16. The AAV2/9 vector of claim 14, wherein the sequence encoding the functional human NMNAT1 is at least 99% identical to SEQ ID NO:1.

17. The AAV2/9 vector of claim 14, wherein the sequence encoding the functional human NMNAT1 comprises SEQ ID NO:1.

18. A pharmaceutical composition comprising the vector of claim 14, formulated for delivery via sub-retinal injection.

* * * * *

SEQUENCE LISTING

<160> NUMBER OF SEQ ID NOS: 6

<210> SEQ ID NO 1
<211> LENGTH: 840
<212> TYPE: DNA
<213> ORGANISM: Artificial
<220> FEATURE:
<223> OTHER INFORMATION: codon optimized NMNAT1 cDNA

<400> SEQUENCE: 1

```
atggaaaatt cagagaaaac tgaagtggtg ctgttggcat gtggatcgtt caacccatc      60 accaacatgc atctgcgcct ctttgaactg gccaaagact acatgaatgg aactggaaga    120
tacactgtgg tcaaaggcat catctcccca gtggggatg catacaagaa gaagggcttg    180
atccctgcct accaccgggt catcatggct gagctggcca ccaagaactc aaaatgggtg    240
gaagtggaca cctgggagtc actgcaaaag gagtggaagg aaaccttaa agtcctgcgg    300 catcaccagg aaaagctgga agcctcggac tgtgaccacc agcagaacag ccccacccct    360
gaacgcccag ggagaaagcg caagtggact gagacccaag actcaagcca gaagaagtcg    420
ctggaaccca agaccaaagc tgtcccaaag gtgaaactcc tctgtggagc tgacctcctg    480
gaatcgtttg ctgtgcctaa tctctggaag tcggaagata tcacccaaat tgtggccaac    540
tatggcctga tctgtgtgac tagagctggt aatgatgccc agaaattcat ctatgaatca    600
gatgtgctgt ggaagcaccg gagcaacatc catgtggtca atgagtggat tgcaaatgac    660
atctcctcca ccaagatcag aagggccctg aggcggggac agtcgatcag gtacttggtc    720
ccagaccttg tccaagagta cattgaaaag cacaacctct acagctcaga gtcagaggat    780
cgcaatgcag gagtgatcct ggccctctc cagcggaaca ctgcagaggc caagacttag    840
```

<210> SEQ ID NO 2
<211> LENGTH: 840
<212> TYPE: DNA
<213> ORGANISM: Homo sapiens

<400> SEQUENCE: 2

```
atggaaaatt ccgagaagac tgaagtggtt ctccttgctt gtggttcatt caatcccatc      60
```

```
accaacatgc acctcaggtt gtttgagctg gccaaggact acatgaatgg aacaggaagg    120
tacacagttg tcaaaggcat catctctcct gttggtgatg cctacaagaa gaaaggactc    180
attcctgcct atcaccgggt catcatggca gaacttgcta ccaagaattc taaatgggtg    240
gaagttgata catgggaaag tcttcagaag gagtggaaag agactctgaa ggtgctaaga    300
caccatcaag agaaattgga ggctagtgac tgtgatcacc agcagaactc acctactcta    360
gaaaggcctg gaaggaagag gaagtggact gaaacacaag attctagtca aaagaaatcc    420
ctagagccaa aacaaaagc tgtgccaaag gtcaagctgc tgtgtggggc agatttattg    480
gagtcctttg ctgttcccaa tttgtggaag agtgaagaca tcacccaaat cgtggccaac    540
tatgggctca tatgtgttac tcgggctgga aatgatgctc agaagtttat ctatgaatcg    600
gatgtgctgt ggaaacaccg gagcaacatt cacgtggtga atgaatggat cgctaatgac    660
atctcatcca caaaaatccg gagagccctc agaaggggcc agagcattcg ctacttggta    720
ccagatcttg tccaagaata cattgaaaag cataatttgt acagctctga gagtgaagac    780
aggaatgctg gggtcatcct ggccccttg cagagaaaca ctgcagaagc taagacatag    840
```

<210> SEQ ID NO 3
<211> LENGTH: 279
<212> TYPE: PRT
<213> ORGANISM: Homo sapiens

<400> SEQUENCE: 3

```
Met Glu Asn Ser Glu Lys Thr Glu Val Val Leu Leu Ala Cys Gly Ser
1               5                   10                  15

Phe Asn Pro Ile Thr Asn Met His Leu Arg Leu Phe Glu Leu Ala Lys
            20                  25                  30

Asp Tyr Met Asn Gly Thr Gly Arg Tyr Thr Val Val Lys Gly Ile Ile
        35                  40                  45

Ser Pro Val Gly Asp Ala Tyr Lys Lys Gly Leu Ile Pro Ala Tyr
    50                  55                  60

His Arg Val Ile Met Ala Glu Leu Ala Thr Lys Asn Ser Lys Trp Val
65                  70                  75                  80

Glu Val Asp Thr Trp Glu Ser Leu Gln Lys Glu Trp Lys Glu Thr Leu
                85                  90                  95

Lys Val Leu Arg His His Gln Glu Lys Leu Glu Ala Ser Asp Cys Asp
            100                 105                 110

His Gln Gln Asn Ser Pro Thr Leu Glu Arg Pro Gly Arg Lys Arg Lys
        115                 120                 125

Trp Thr Glu Thr Gln Asp Ser Ser Gln Lys Lys Ser Leu Glu Pro Lys
130                 135                 140

Thr Lys Ala Val Pro Lys Val Lys Leu Leu Cys Gly Ala Asp Leu Leu
145                 150                 155                 160

Glu Ser Phe Ala Val Pro Asn Leu Trp Lys Ser Glu Asp Ile Thr Gln
                165                 170                 175

Ile Val Ala Asn Tyr Gly Leu Ile Cys Val Thr Arg Ala Gly Asn Asp
            180                 185                 190

Ala Gln Lys Phe Ile Tyr Glu Ser Asp Val Leu Trp Lys His Arg Ser
        195                 200                 205

Asn Ile His Val Val Asn Glu Trp Ile Ala Asn Asp Ile Ser Ser Thr
    210                 215                 220

Lys Ile Arg Arg Ala Leu Arg Arg Gly Gln Ser Ile Arg Tyr Leu Val
225                 230                 235                 240
```

```
Pro Asp Leu Val Gln Glu Tyr Ile Glu Lys His Asn Leu Tyr Ser Ser
                245                 250                 255

Glu Ser Glu Asp Arg Asn Ala Gly Val Ile Leu Ala Pro Leu Gln Arg
            260                 265                 270

Asn Thr Ala Glu Ala Lys Thr
        275

<210> SEQ ID NO 4
<211> LENGTH: 18
<212> TYPE: DNA
<213> ORGANISM: Artificial
<220> FEATURE:
<223> OTHER INFORMATION: forward primer intron 1

<400> SEQUENCE: 4
catggctgtg ctgaggtg                                                18

<210> SEQ ID NO 5
<211> LENGTH: 20
<212> TYPE: DNA
<213> ORGANISM: Artificial
<220> FEATURE:
<223> OTHER INFORMATION: reverse primer exon 2

<400> SEQUENCE: 5
aacagcctga ggtgcatgtt                                              20

<210> SEQ ID NO 6
<211> LENGTH: 20
<212> TYPE: DNA
<213> ORGANISM: Artificial
<220> FEATURE:
<223> OTHER INFORMATION: sequencing primer

<400> SEQUENCE: 6
acgtatttgc ccacctgtct                                              20
```